United States Patent
Shimoda et al.

(10) Patent No.: US 11,572,331 B2
(45) Date of Patent: Feb. 7, 2023

(54) QUATERNARY ALKYL AMMONIUM HYPOCHLORITE SOLUTION, METHOD OF PRODUCING THE SAME, AND METHOD FOR PROCESSING SEMICONDUCTOR WAFERS

(71) Applicant: TOKUYAMA CORPORATION, Yamaguchi (JP)

(72) Inventors: Takafumi Shimoda, Yamaguchi (JP); Yuki Kikkawa, Yamaguchi (JP); Tomoaki Sato, Yamaguchi (JP); Takayuki Negishi, Yamaguchi (JP)

(73) Assignee: TOKUYAMA CORPORATION, Yamaguchi (JP)

( * ) Notice: Subject to any disclaimer, the term of this patent is extended or adjusted under 35 U.S.C. 154(b) by 0 days.

(21) Appl. No.: 17/838,536

(22) Filed: Jun. 13, 2022

(65) Prior Publication Data

US 2022/0315522 A1    Oct. 6, 2022

Related U.S. Application Data

(63) Continuation of application No. 16/953,754, filed on Nov. 20, 2020, now Pat. No. 11,390,577.

(30) Foreign Application Priority Data

Nov. 22, 2019 (JP) .............. JP2019-211879

(51) Int. Cl.
*C07C 209/68* (2006.01)
*C11D 3/395* (2006.01)
(Continued)

(52) U.S. Cl.
CPC .............. *C07C 209/68* (2013.01); *B08B 3/08* (2013.01); *C11D 3/3955* (2013.01); *C11D 11/0047* (2013.01); *H01L 21/02057* (2013.01)

(58) Field of Classification Search
CPC ..................................................... C07C 209/68
See application file for complete search history.

(56) References Cited

U.S. PATENT DOCUMENTS

| | | | |
|---|---|---|---|
| 7,521,406 B2 | 4/2009 | Hsu | |
| 2002/0060202 A1 | 5/2002 | Fukunaga et al. | |

(Continued)

FOREIGN PATENT DOCUMENTS

| | | |
|---|---|---|
| JP | 2002-161381 | 6/2002 |
| JP | 2003-119494 | 4/2003 |

(Continued)

*Primary Examiner* — Amanda C. Walke
(74) *Attorney, Agent, or Firm* — Wenderoth, Lind & Ponack, L.L.P.

(57) ABSTRACT

Provided is a method of producing a quaternary alkyl ammonium hypochlorite solution with an excellent storage stability. Specifically, provided is a method of producing a quaternary alkyl ammonium hypochlorite solution, the method including: a preparation step in which a quaternary alkyl ammonium hydroxide solution is prepared and the concentration of amines in the quaternary alkyl ammonium hydroxide solution is set to 20 ppm by mass or less; and a reaction step in which the quaternary alkyl ammonium hydroxide solution is brought into contact with chlorine gas, wherein the concentration of carbon dioxide of a gas phase in the reaction step is 100 ppm by volume or less and the pH of a liquid phase in the reaction step is 10.5 or more.

12 Claims, 2 Drawing Sheets

(51) Int. Cl.
    *C11D 11/00*     (2006.01)
    *B08B 3/08*     (2006.01)
    *H01L 21/02*     (2006.01)

(56) References Cited

U.S. PATENT DOCUMENTS

2005/0176603 A1    8/2005    Hsu
2021/0309942 A1    10/2021    Shimoda et al.

FOREIGN PATENT DOCUMENTS

JP    2005-227749    8/2005
JP    2009-81247    4/2009

QUATERNARY ALKYL AMMONIUM HYPOCHLORITE SOLUTION, METHOD OF PRODUCING THE SAME, AND METHOD FOR PROCESSING SEMICONDUCTOR WAFERS

BACKGROUND OF THE INVENTION

Field of the Invention

The present invention relates to a quaternary alkyl ammonium hypochlorite solution and a method of producing the same. More specifically, the present invention relates to a quaternary alkyl ammonium hypochlorite solution with excellent storage stability and a method of producing the same. This invention relates to a quaternary alkyl ammonium hypochlorite solution with reduced metal impurities suitable for cleaning semiconductor wafers and elements, and a method of producing the same.

In recent years, as the design rules of semiconductor devices have become finer and finer, impurity control in manufacturing processes of semiconductor devices are highly demanded. It is important to identify the source of contamination and then control the concentration of an impurity as a source of contamination in each manufacturing process, since impurities generated in manufacturing processes of semiconductor devices are different from each other.

In order to improve manufacturing efficiency of semiconductor devices, semiconductor wafers with a large diameter of over 300 mm are used. In large-diameter semiconductor wafers, the area of the end face or back surface, where electronic devices are not fabricated, is larger than that in small-diameter semiconductor wafers. Therefore, in a process of forming metal wiring or forming a barrier metal, the metal wiring material or barrier metal material (hereinafter, collectively referred to as "metal materials, or the like" in some cases) tends to adhere not only to the surface of a semiconductor wafer on which semiconductor devices are formed, but also to the end face or back surface of the semiconductor wafer. Consequently, large-diameter semiconductor wafers have an increased amount of excess metal and other materials that adhere to the end face or back surface compared to small-diameter wafers.

Excess metal materials, or the like deposited on the end face or back face of semiconductor wafers can contaminate manufacturing equipment as metal or metal oxide particles in an oxygen ashing step or a plasma dry etching step that follows the formation of metal wiring or barrier metal, causing cross-contamination. Therefore, metal materials, or the like that adhered to the end face or back surface needed to be removed before being brought to the next step.

Among these metal materials, noble metals such as platinum and ruthenium are difficult to be oxidized, dissolved, or removed in a subsequent etching or cleaning step. Therefore, these noble metals are preferably removed from a semiconductor wafer in preference to other metal materials. In particular, since ruthenium is often used as a wiring material for semiconductor devices with a design rule of 10 nm or less, due to the ability to reduce the resistance value compared to the case of using copper as a wiring material, it is desirable to quickly remove ruthenium from unwanted areas.

In general, a cleaning method utilizing hypochlorite which has high oxidation power as a cleaning liquid for semiconductor wafers has been proposed. Specifically, a method using a sodium hypochlorite solution has been proposed (see Patent Documents 1 and 2).

However, in the method of using a sodium hypochlorite solution as a cleaning liquid, the amount of sodium ions in the cleaning liquid inevitably increases. As a result, sodium ions tend to adhere to semiconductor wafers or the like, which may deteriorate production efficiency of semiconductors.

In contrast, cleaning liquids using hypochlorous acid solutions (see Patent Document 3) or quaternary alkyl ammonium hypochlorite solutions (see Patent Document 4), in which sodium is not an essential component, have also been developed.

However, these cleaning liquids using hypochlorous acid (see Patent Document 3) are used for cleaning a substrate equipped with a metal film or a metal oxide film, and are not specifically intended for removal of noble metals. Therefore, these cleaning liquids are not suitable for cleaning metal/metal oxide films of noble metals or the like.

On the other hand, the cleaning liquid containing tetramethylammonium hypochlorite solution described in Patent Document 4 is also a cleaning liquid used for cleaning photoresists or residues, and is not intended for cleaning metallic coating of copper or aluminum containing ruthenium. Examples specifically illustrate that metal films are difficult to etch.

| Citation List | |
|---|---|
| Patent Documents | |
| Patent Document 1 | Japanese Unexamined Patent Application Publication No. 2002-161381 |
| Patent Document 2 | Japanese Unexamined Patent Application Publication No. 2009-081247 |
| Patent Document 3 | Japanese Unexamined Patent Application Publication No. 2003-119494 |
| Patent Document 4 | Japanese Unexamined Patent Application Publication No. 2005-227749 |

SUMMARY OF THE INVENTION

The storage stability of the tetramethylammonium hypochlorite solution of Patent Document 4 is not necessarily satisfactory. In other words, it was found by the present inventors that a desired cleaning performance was not achieved due to a decrease in hypochlorite ions, which exert an oxidizing effect, over time.

Patent Document 4 discloses addition of, for example, a triazole, a thiazole, a tetrazole, and an imidazole as a stabilizer to a cleaning composition in order to maintain the level of available halogens.

However, added stabilizers tend to remain as organic residue after cleaning, causing reduction in yield of semiconductor devices. Stabilizers tend to adsorb on certain metals, for example, triazoles tend to adsorb on copper, which may reduce ability to clean copper.

Therefore, a first object of the present invention is to provide a method of producing a quaternary alkyl ammonium hypochlorite solution with a low change in hypochlorite ion concentration over time and excellent storage stability without addition of a stabilizer.

The cleaning liquid containing a tetramethylammonium hypochlorite solution described in Patent Document 4 is for removing photoresist/residue, as described above. For this reason, for example, reducing the metal content of sodium, aluminum, and/or potassium in the cleaning liquid is not considered. It is believed that the production efficiency of semiconductor devices can be improved if the metal content in the cleaning liquid is reduced.

Accordingly, a second object of the present invention is to provide a quaternary alkyl ammonium hypochlorite solution with a reduced metal content used in a process for manufacturing semiconductor devices, and a method of producing the solution.

Solution to Problem

The present inventors have diligently studied to achieve the above-described first object. The present inventors then found that because the pH of the quaternary alkyl ammonium hypochlorite solution during reaction was not controlled, the concentration of hypochlorite ions present in the quaternary alkyl ammonium hypochlorite solution was reduced, and the cleaning power and removing power of the solution was reduced.

In other words, the concentration of hypochlorite ion varies greatly depending on the pH of a quaternary alkyl ammonium hypochlorite solution in a reaction step. As a result of further investigation of factors of pH fluctuation in the reaction step, it was found that the pH of the reaction solution fluctuated greatly due to absorption of carbon dioxide in a gas phase of the reaction step into the reaction solution, and that a quaternary alkyl ammonium hypochlorite solution with high storage stability could be produced by controlling the concentration of carbon dioxide in a gas phase of the reaction step without adding a stabilizer.

After further investigation based on the above-described findings, it was found that a quaternary alkyl ammonium hypochlorite solution, which can be suitably used as an oxidizer or detergent, can be further improved in storage stability by adjusting the pH of the quaternary alkyl ammonium hypochlorite solution without addition of a stabilizer.

In other words, it was found that the reaction rates of disproportionation reactions of hypochlorous acid and hypochlorite ions differed depending on the pH of a quaternary alkyl ammonium hypochlorite solution, and that there was a pH range in which the autolysis of the hypochlorous acid and hypochlorite ions was inhibited. It is generally known that the disproportionation reaction of hypochlorous acid and hypochlorite ions is inhibited in sodium hypochlorite solution in alkaline conditions, for example, at pH 11 or higher, and in the case of quaternary alkyl ammonium hypochlorite solution, the disproportionation reaction of hypochlorous acid and hypochlorite ions is specifically inhibited at a pH of 12 or more and less than 14.

For example, when the quaternary alkyl ammonium hypochlorite solution of the present invention is used for cleaning and removing metals, the optimal pH of the quaternary alkyl ammonium hypochlorite solution is more than 7 and less than 12, and it was found by the present inventor that when the quaternary alkyl ammonium hypochlorite solution was prepared and stored in such a pH range, the oxidation power of the solution was considerably lost in a short time.

The inventors examined to find that ammonia or amines present in a quaternary alkyl ammonium hydroxide solution and/or a quaternary alkyl ammonium hypochlorite solution adversely affected the hypochlorite ion concentration and the stability of the quaternary alkyl ammonium hypochlorite solution. The present inventors further studied to find that reduction of ammonia and amines in a quaternary alkyl ammonium hydroxide solution and/or a quaternary alkyl ammonium hypochlorite solution in a preparation step, a reaction step, and a storage step inhibited a decrease in the concentration of the hypochlorite ions and improved the stability of the quaternary alkyl ammonium hypochlorite solution.

Based on these findings, the present inventors found that the concentration of hypochlorite ions did not decrease and that the storage stability of the quaternary alkyl ammonium hypochlorite solution was improved, by adjusting the pH of a quaternary alkyl ammonium hypochlorite solution without addition of a stabilizer, or by reducing ammonia and amines contained in a quaternary alkyl ammonium hydroxide solution and/or a quaternary alkyl ammonium hypochlorite solution.

The present inventors diligently studied to achieve the above-described second objective. First, possible metal impurities contained in the quaternary alkyl ammonium hypochlorite solution described in Patent Document 4 were studied in detail.

In Patent Document 4, the need to reduce metal atoms contained in a tetramethylammonium hypochlorite solution is not considered because removal of a photoresist is the objective.

Specifically, in Examples of Patent Document 4, tetramethylammonium hypochlorite solution is produced by reacting a tetramethylammonium hydroxide solution with chlorine gas in an Erlenmeyer flask. The flask is highly probable to be a glass vessel since the flask is not specified in any way. The present inventors found in a follow-up test of the Examples that resulting quaternary alkyl ammonium hypochlorite solution contained relatively more metal atoms such as sodium.

Accordingly, the present inventors studied reasons for the inclusion of metallic atoms such as sodium. One of the reasons was attributed to a quaternary alkyl ammonium hydroxide as a raw material and the material of the flask. Specifically, it was assumed that since quaternary alkyl ammonium hydroxide is a strong alkaline substance, the inclusion is caused by dissolution of metal atoms such as sodium from the glass material of the flask. It was then found that the above-described problem could be solved by limiting the material of a reaction vessel when a quaternary alkyl ammonium hydroxide solution was reacted with chlorine gas.

Specifically, the present invention is composed as follows.

Aspect 1 A method of producing a quaternary alkyl ammonium hypochlorite solution, the method including: a preparation step in which a quaternary alkyl ammonium hydroxide solution is prepared and the concentration of amines in the quaternary alkyl ammonium hydroxide solution is set to 20 ppm by mass or less; and a reaction step in which the quaternary alkyl ammonium hydroxide solution is brought into contact with chlorine gas, wherein the concentration of carbon dioxide of a gas phase in the reaction step is 100 ppm by volume or less and the pH of a liquid phase in the reaction step is 10.5 or more.

Aspect 2 The method of producing a quaternary alkyl ammonium hypochlorite solution according to Aspect 1, wherein chlorine gas is contacted while maintaining the concentration of amines contained in the liquid phase in the reaction step at 100 ppm by mass or less.

Aspect 3 The method of producing a quaternary alkyl ammonium hypochlorite solution according to Aspect 1 or 2, wherein the carbon dioxide concentration in the quaternary alkyl ammonium hydroxide solution is 0.001 ppm by mass or more and 500 ppm by mass or less.

Aspect 4 The method of producing a quaternary alkyl ammonium hypochlorite solution according to any one of Aspects 1 to 3, wherein the water content of the chlorine gas is 10 ppm by volume or less.

Aspect 5 The method of producing a quaternary alkyl ammonium hypochlorite solution according to any one of Aspects 1 to 4, wherein the reaction temperature is −35° C. or more and 25° C. or less in the reaction step.

Aspect 6 The method of producing a quaternary alkyl ammonium hypochlorite solution according to any one of Aspects 1 to 5, wherein the quaternary alkyl ammonium hydroxide solution prepared in the preparation step is a solution of a quaternary alkyl ammonium hydroxide in which the number of carbon atoms of the alkyl group is from 1 to 10.

Aspect 7 The method of producing a quaternary alkyl ammonium hypochlorite solution according to any one of Aspects 1 to 6, wherein the reaction step is a step of bringing a quaternary alkyl ammonium hydroxide solution into contact with chlorine gas in a reaction vessel, wherein the surface of the reaction vessel in contact with the quaternary alkyl ammonium hydroxide solution is made of an organic polymer material, and the reaction vessel is shielded from light.

Aspect 8 The method of producing a quaternary alkyl ammonium hypochlorite solution according to Aspect 7, wherein the organic polymer material is a fluororesin.

Aspect 9 The method of producing a quaternary alkyl ammonium hypochlorite solution according to any one of Aspects 1 to 8, the method further including a filtration step in which a quaternary alkyl ammonium hypochlorite solution is obtained by the production method according to Aspects 1 to 8, and then the resulting quaternary alkyl ammonium hypochlorite solution is filtered.

Aspect 10 The method according to Aspect 9, wherein the pH of a quaternary alkyl ammonium hypochlorite solution in a filtration step at 25° C. is 13.5 or less.

Aspect 11 The method of producing a quaternary alkyl ammonium hypochlorite solution according to any one of Aspects 1 to 10, the method including a storage step in which a quaternary alkyl ammonium hypochlorite solution is obtained by the production method according to Aspects 1 to 10, and the resulting quaternary alkyl ammonium hypochlorite solution is stored under shade of light with a pH of the quaternary alkyl ammonium hypochlorite solution is 12.0 or more and less than 14.0 at 25° C.

Aspect 12 The method of producing a quaternary alkyl ammonium hypochlorite solution according to Aspect 11, wherein the concentration of amines in a quaternary alkyl ammonium hypochlorite solution is stored at a concentration of 100 ppm by mass or less in the storage step.

Aspect 13 A method for processing a semiconductor wafer, in which a surface of the semiconductor wafer is treated with a quaternary alkyl ammonium hypochlorite solution obtained by the method according to any one of Aspects 1 to 12.

Aspect 14 The method for processing according to Aspect 13, wherein the semiconductor wafer is a semiconductor wafer containing at least one selected from the group consisting of copper, tungsten, tantalum, titanium, cobalt, ruthenium, manganese, aluminum, silicon, silicon oxide, and a compound thereof.

According to the production method of the present invention described above, a quaternary alkyl ammonium hypochlorite solution with high storage stability can be produced without addition of a stabilizer such as triazole, thiazole, tetrazole, or imidazole. A quaternary alkyl ammonium hypochlorite solution thus obtained does not need addition of a stabilizer that is not involved in the cleaning ability. Therefore, the quaternary alkyl ammonium hypochlorite solution produced by the present invention can be suitably used as a cleaning liquid that does not reduce the yield when used in a semiconductor manufacturing process. Furthermore, a quaternary alkyl ammonium hypochlorite solution with a low metal content can be obtained. Therefore, such a solution can be suitably used as an etching liquid or a cleaning liquid used in manufacturing semiconductor devices.

By including the filtration step described above, the metal content in a quaternary alkyl ammonium hypochlorite solution can be further reduced. Furthermore, the storage stability can be further improved by controlling the pH at the time of storage under shade of light.

Effects achieved by embodiments of the present invention will be described in further detail below.

Figure 1:
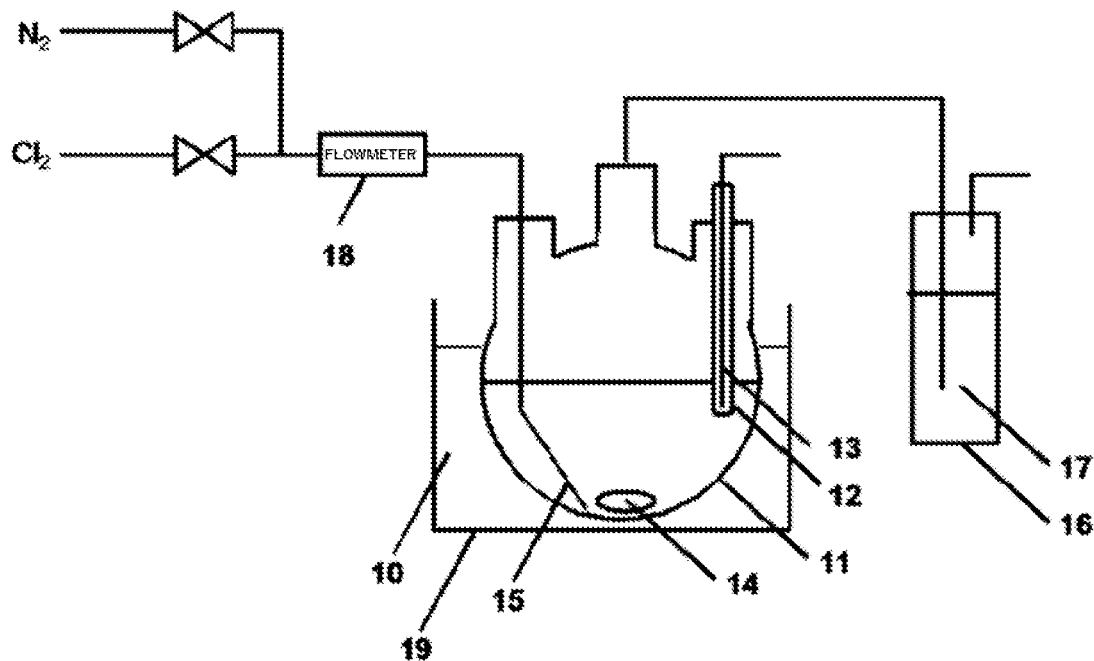
FIG. 1 is a schematic diagram illustrating a method of producing a quaternary alkyl ammonium hypochlorite solution according to a first embodiment.

DESCRIPTION OF THE EMBODIMENTS (Production Method of Quaternary Alkyl Ammonium Hypochlorite Solution)

The method of producing a quaternary alkyl ammonium hypochlorite solution according to the present invention includes: a preparation step in which a quaternary alkyl ammonium hydroxide solution is prepared and the concentration of amines in the quaternary alkyl ammonium hydroxide solution is set to 20 ppm by mass or less; and a reaction step in which the quaternary alkyl ammonium hydroxide solution is brought into contact with chlorine gas, and is characterized in that the concentration of carbon dioxide of a gas phase in the reaction step is 100 ppm by volume or less and the pH of a liquid phase in the reaction step is 10.5 or more. Each step is described below.

(Preparation Step in which Quaternary Alkyl Ammonium Hydroxide Solution is Prepared)

The quaternary alkyl ammonium hydroxide solution may be any of an aqueous solution in which a quaternary alkyl ammonium hydroxide is dissolved in water or a solution in which a quaternary alkyl ammonium hydroxide is dissolved in a nonaqueous solvent. A quaternary alkyl ammonium hydroxide solution can be obtained by dissolving a quaternary alkyl ammonium hydroxide in water or a nonaqueous solvent or by diluting a commercially available quaternary alkyl ammonium hydroxide solution to a desired concentration. Examples of non-aqueous solvents include known organic solvents capable of dissolving the quaternary alkyl ammonium hydroxide. Specific examples thereof include alcohols and glycols, and methanol and propylene glycol are particularly preferred. Among these solvents, water is preferred because water is industrially easy to obtain and because a high purity quaternary alkyl ammonium hydroxide solution can be obtained.

Although the concentration of the quaternary alkyl ammonium hydroxide solution is not particularly limited, when the concentration of the quaternary alkyl ammonium hydroxide becomes high, a salt is precipitated and the solution becomes solid. Therefore, the concentration of the quaternary alkyl ammonium hydroxide solution is preferably from 0.01 to 30% by mass, more preferably from 0.05 to 27.5% by mass, and still more preferably from 0.1 to 25% by mass.

A quaternary alkyl ammonium hydroxide solution to be prepared contains carbon dioxide, which is usually derived from the atmosphere. Carbon dioxide is present in the solution as carbonate ions or bicarbonate ions. The carbon dioxide concentration is not particularly restricted, and is preferably 0.001 ppm or more and 500 ppm or less (based on mass), more preferably 0.005 ppm or more and 300 ppm or less, and still more preferably 0.01 ppm or more and 100 ppm or less, in terms of carbonate ions. When the carbon dioxide concentration in the quaternary alkyl ammonium hydroxide solution is 0.001 ppm or more and 500 ppm or less, the pH change of the resulting quaternary alkyl ammonium hypochlorite solution can be controlled. As a result, the storage stability of the quaternary alkyl ammonium hypochlorite solution can be improved. For a quaternary alkyl ammonium hydroxide solution with such a carbon dioxide concentration, a commercially available one can be utilized.

The presence of ammonia and/or amines in a quaternary alkyl ammonium hydroxide solution to be prepared results in decomposition of hypochlorite ions produced in the reaction step. In general, commercially available quaternary alkyl ammonium hydroxide solutions contain amines. When such a quaternary alkyl ammonium hydroxide solution is used, amines react with the hypochlorite ions generated in the reaction step and cause a decrease in the concentration of hypochlorite ions.

Furthermore, when the amines are tertiary amines, secondary amines, primary amines, and ammonia, which are produced by the reaction with hypochlorite ion, also react with hypochlorite ions and thus cause a significant decrease in the concentration of hypochlorite ions. In particular, tertiary amines react rapidly with hypochlorite ions, and even the presence of a small amount of tertiary amines causes a significant decrease in the concentration of hypochlorite ions. For example, commercially available tetramethylammonium hydroxide solutions are known to contain from several tens to several hundreds of parts per million by mass of trimethylamine. Since trimethylamine reacts with hypochlorite ions to produce dimethylamine and monomethylamine, the use of such tetramethylammonium hydroxide solutions is not appropriate because of a decrease in the concentration of hypochlorite ions.

Accordingly, the concentration of ammonia and/or amines in the quaternary alkyl ammonium hydroxide solution is preferably small, and specifically, the concentration is preferably 20 ppm by mass or less. When the concentration is 20 ppm by mass or less, decrease in the concentration of hypochlorite ions produced in the reaction step can be minimized, and the stability of the obtained quaternary ammonium hypochlorite solution can be increased. Therefore, the preparation step in the production method of the present invention is characterized in that the concentration of amines contained in the quaternary alkyl ammonium hydroxide solution is 20 ppm by mass or less. In other words, the concentration of amines contained in the quaternary alkyl ammonium hydroxide solution that has undergone the preparation step is 20 ppm by mass or less. In the present invention, the concentration of amines is the sum of the concentrations of tertiary amines, secondary amines, primary amines, and ammonia in the solution. The concentration of amines in the solution can be determined by widely known methods, such as gas chromatography, liquid chromatography, colorimetric analysis, mass spectrometry, and an analytical method combining these methods.

When the concentration of amines in the quaternary alkyl ammonium hydroxide solution exceeds 20 ppm by mass, the concentration of the amines in the quaternary alkyl ammonium hydroxide solution can be reduced to 20 ppm by mass or less by using a method that allows the concentration of amines to be reduced. The quaternary alkyl ammonium hydroxide solution thus obtained can be suitably used in the production method of the present invention.

Examples of the methods for reducing the concentration of amines in the quaternary alkyl ammonium hydroxide solution include removal of ammonia and/or amines by heating, distillation, or ion exchange of the tetramethylammonium hydroxide solution, removal of ammonia and/or amines by decompression treatment, degassing treatment, or passing of inert gas, and any method may be used as long as the concentration of the amines can be reduced. The above-described methods for reducing the concentration of amines may be performed singly or in combination.

As a matter of course, by subjecting a quaternary alkyl ammonium hydroxide solution in which the concentration of amines is 20 ppm by mass or less to a further ammonia and/or amines removal operation such as heating, distillation, ion exchange, decompression treatment, degassing, passing of inert gas, the concentration of amines can be lowered. The quaternary alkyl ammonium hydroxide solution thus obtained can be more suitably used in the production method of the present invention.

In general, the concentration of amines in the tetramethylammonium hydroxide solution for semiconductor applications is lower than the concentration of amines in the tetramethylammonium hydroxide solution used for industrial applications. Therefore, it is preferable to use tetramethylammonium hydroxide solution for semiconductor applications as the tetramethylammonium hydroxide solution used in the production method of the present invention. In cases in which such a tetramethylammonium hydroxide solution is used, when the concentration of amines in the tetramethylammonium hydroxide solution is 20 ppm by mass or less, the reaction step can be carried out without a removal operation of ammonia and/or amines. Such cases are also included in the preparation step of the present invention.

As a solvent for preparing a quaternary alkyl ammonium hydroxide solution, an aqueous solution using only water as the solvent may be prepared, or a non-aqueous solution may be prepared by mixing an organic solvent. The solvent may be changed appropriately depending on the application of the quaternary alkyl ammonium hypochlorite solution and an object to be cleaned. For example, when an object to be cleaned is ruthenium, only water as a solvent is sufficient for cleaning, and therefore, a quaternary alkyl ammonium hydroxide aqueous solution can be prepared.

In the production method of the present invention, the quaternary alkyl ammonium hydroxide solution is preferably a solution of a quaternary alkyl ammonium hydroxide in which the number of carbon atoms of the alkyl group is from 1 to 10, and more preferably a solution of a quaternary alkyl ammonium hydroxide in which the number of carbon atoms of the alkyl group is from 1 to 5. Specific examples of quaternary alkyl ammonium hydroxide include tetramethyl ammonium hydroxide, tetraethyl ammonium hydroxide, tetrapropyl ammonium hydroxide, and tetrabutyl ammonium hydroxide. These quaternary alkyl ammonium hydroxides may be used singly or in combination with two or more kinds thereof. The number of carbon atoms of the four alkyl groups in the quaternary alkyl ammonium hydroxide may be the same or different from each other.

In a step of producing a quaternary alkyl ammonium hypochlorite solution by reacting a quaternary alkyl ammonium hydroxide solution with chlorine gas, the pH of a solution containing the quaternary alkyl ammonium hypochlorite solution generated in a reaction vessel is lowered. Considering the conditions of filtration operation described below and the solubility of a quaternary alkyl ammonium hydroxide, in the present embodiment, the lower limit of the pH of the quaternary alkyl ammonium hydroxide solution as a raw material is 10.5 or more, and the upper limit is determined by the concentration of the quaternary alkyl ammonium hydroxide.

The quaternary alkyl ammonium hydroxide solution used in the production method of the present invention preferably has contents of metals, specifically, sodium, potassium, aluminum, magnesium, iron, nickel, copper, silver, cadmium, and lead of 0.01 ppb or more and 20 ppb or less, respectively. As a matter of course, the metal content in the quaternary alkyl ammonium hydroxide solution to be used may be less than 0.01 ppb, but such a quaternary alkyl ammonium hydroxide solution itself is difficult to obtain.

Therefore, by using a quaternary alkyl ammonium hydroxide solution with a metal content satisfying the above-described range, it is easy to obtain the solution itself and to remove or reduce the metal impurities by filtration operations during and after production of the quaternary alkyl ammonium hypochlorite solution. The reason why the metal impurities can be removed or reduced by filtration is not clear, but it is believed that the presence of a certain amount of metal impurities produces not colloidal impurity particles, which are difficult to remove by filtration, but impurity particles having a certain size, which can be removed by filtration. Therefore, the quaternary alkyl ammonium hydroxide solution used in the present embodiment can be suitably used even when the solution is not an ultra-pure quaternary alkyl ammonium hydroxide solution, because solid metal impurities can be removed or reduced by filtration operations due to a decrease in pH. In order to enhance this effect and to further remove or reduce impurities, especially those that are ionic in alkali, each content of metals of sodium, potassium, aluminum, magnesium, iron, nickel, copper, silver, cadmium, and lead in the quaternary alkyl ammonium hydroxide solution is more preferably 0.01 ppb or more and 5 ppb or less, and still more preferably 0.01 ppb or more and 2 ppb or less.

For the above-described quaternary alkyl ammonium hydroxide solution, a commercially available one can be used. Among them, a quaternary alkyl ammonium hydroxide solution used as a photoresist developer for semiconductor devices, which has been purified by the electrolysis method and/or by contacting with an ion exchange resin or the like, can be suitably used. These commercially available solutions can also be used after being diluted with a solvent that does not contain metal impurities, such as ultrapure water.

(Reaction Step of Contacting Quaternary Alkyl Ammonium Hydroxide Solution with Chlorine Gas)

By contacting and reacting a quaternary alkyl ammonium hydroxide solution with chlorine gas, hydroxide ions of quaternary alkyl ammonium hydroxide are replaced with hypochlorite ions produced by chlorine gas to produce a quaternary alkyl ammonium hypochlorite solution.

(Chlorine Gas)

The chlorine gas to be used in the production method of the present invention is not particularly restricted, and commercially available chlorine gas can be employed. Among them, a high purity gas such as those used for etching semiconductor materials and as a raw material for semiconductor materials can be used.

Among high purity gases, one with a low water content is particularly preferred, and specifically, one with a water content of 10 ppm by volume or less is preferably used. The reason for this is not clear, but the following is possible. For example, when producing a quaternary alkyl ammonium hypochlorite solution, a chlorine gas is usually transported through pipes. Therefore, when there is a large amount of water, hydrogen chloride is generated and corrodes metal members of the pipes, flowmeter, and the like, and the corroded metal impurities are easily introduced into a system with the chlorine gas. Therefore, it is preferable to use chlorine gas with a water content of 10 ppm by volume or less. As a matter of course, when the water content in a commercially available chlorine gas is 10 ppm by volume or less, the gas can be used as it is, or the water content in the chlorine gas can be reduced by contacting the gas with a desiccant material or the like immediately before being introduced into a reaction system. The lower limit of the amount of water contained in the chlorine gas is not particularly restricted, but considering the industrial availability of the gas, the amount is 0.1 ppm by volume.

Although the concentration of carbon dioxide in the chlorine gas is not particularly restricted, the concentration is preferably 0.001 ppm by volume or more and 80 ppm by volume or less, more preferably 0.005 ppm by volume or more and 50 ppm by volume or less, and still more preferably 0.01 ppm by volume or more and 2 ppm by volume or less. When the carbon dioxide concentration in the chlorine gas is 0.001 ppm by volume or more and 80 ppm by volume or less, the pH change in the resulting quaternary alkyl ammonium hypochlorite solution can be controlled. As a result, the storage stability of the quaternary alkyl ammonium hypochlorite solution can be improved. For chlorine gas with such a carbon dioxide concentration, a commercially available one can be utilized.

Although the amount of chlorine gas used (the total amount of chlorine gas used) is not particularly restricted, the amount is preferably from 10 to 31,000 mL in terms of 0° C. and 1 atm for 1 liter of quaternary alkyl ammonium hydroxide solution. By using chlorine gas in this range, a sudden change in pH in a reaction system is controlled, and removal and reduction of metal impurities by filtration operations is facilitated. For 1 liter of quaternary alkyl ammonium hydroxide solution, the amount of chlorine gas used can be greater than 31,000 mL at 0° C. and 1 atm, but the pH of the quaternary alkyl ammonium hydroxide solution tends to fall and fluctuate significantly, and furthermore, unreacted chlorine gas tends to remain. On the other hand, when the amount is less than 10 mL, sufficient hypochlorite ions tend not to be generated. Therefore, considering industrial production, the amount of chlorine gas used for 1 liter of quaternary alkyl ammonium hydroxide solution is preferably in the range of from 10 to 31,000 mL in terms of 0° C. and 1 atm. Note, however, that the amount of chlorine gas used can also be determined in the pH of the resulting solution, or the pH of the resulting quaternary alkyl ammonium hypochlorite solution.

Chlorine gas is preferably supplied to a reaction system at the following rates. The supply rate of chlorine gas is preferably 0.0034 Pa·m$^3$/sec or more and 16.9 Pa·m$^3$/sec or less in terms of 0° C. and 1 atm for 1 liter of quaternary alkyl ammonium hydroxide solution from the viewpoint of not causing a sudden drop in pH and reducing chlorine gas not involved in the reaction. By satisfying this range, the reactivity is sufficient to produce a quaternary alkyl ammonium hypochlorite solution without a sudden drop or fluctuation in pH. In order to further demonstrate this effect, the amount of chlorine gas supplied into the reaction system is more preferably 0.017 Pa·m³/sec or more and 5.1 Pa·m³/sec or less, and still more preferably 0.034 Pa·m³/sec or more 1.7 Pa·m³/sec or less. Note that 1 Pa·m³/sec is equivalent to 592 sccm.

In the production method of the present invention, the method of contacting a quaternary alkyl ammonium hydroxide solution with chlorine gas is not particularly restricted, and known methods can be employed. However, it is preferable to perform a reaction in a closed system to avoid contamination of carbon dioxide into the reaction system. In a simplified manner, as shown in FIG. 1, a quaternary alkyl ammonium hydroxide solution prepared in a three-necked flask can be fully reacted by blowing chlorine gas into the quaternary alkyl ammonium hydroxide solution, to produce a quaternary alkyl ammonium hypochlorite solution with excellent storage stability. A reaction apparatus with the configuration shown in FIG. 2 may be used, as described in detail below.

Furthermore, the step of bringing a quaternary alkyl ammonium hydroxide solution in contact with chlorine gas is preferably carried out using a reaction vessel shaded from light. The above-described chlorine gas present in the reaction vessel may be excited by light to generate chlorine radicals. The generation of chlorine radicals may affect a quaternary alkyl ammonium hydroxide present in the reaction vessel and the above-described quaternary alkyl ammonium hypochlorite generated in the reaction to cause decomposition, and it is desirable to shade the reaction vessel, attached piping, and the like from the light.

Furthermore, a surface in the above-described reaction vessel with which the quaternary alkyl ammonium hydroxide solution is in contact (hereinafter simply referred to as "inner surface of a reaction vessel") is preferably made of an organic polymer material. According to a study by the present inventors, when a general-purpose borosilicate glass (hereinafter "glass") reaction vessel is used as a reaction vessel, a quaternary alkyl ammonium hydroxide solution used as a raw material dissolves the metallic components contained in the glass material, such as sodium, potassium, and aluminum. This may be due to the alkalinity of the quaternary alkyl ammonium hydroxide solution used as a raw material. Therefore, by forming the inner surface of the reaction vessel with an organic polymer material, contamination of impurities including the above-described metals (metal impurities) can be reduced.

Examples of organic polymer materials used in the present embodiment include vinyl chloride resins (soft and hard vinyl chloride resins), nylon-based resins, silicone-based resins, polyolefin resins (polyethylene, polypropylene), and fluororesins. Among them, fluororesins are selected in view of ease of molding, solvent resistance, and low impurity elution.

The fluororesin is not particularly restricted as long as the resin (polymer) contains a fluorine atom, and a known fluororesin can be used. Examples thereof include polytetrafluoroethylene, polychlorotrifluoroethylene, polyvinylidene fluoride, tetrafluoroethylene-hexafluoropropylene copolymers, tetrafluoroethylene-perfluoroalkyl vinyl ether copolymers, tetrafluoroethylene-ethylene copolymers, chlorotrifluoroethylene-ethylene copolymers, and cyclic polymers of perfluoro (butenyl vinyl ether). Among them, a tetrafluoroethylene-perfluoroalkyl vinyl ether copolymer is preferably used in consideration of availability and productivity of a reaction vessel itself.

In the present embodiment, examples of the method of forming the inner surface of a reaction vessel with an organic polymer material includes a method of forming the entire reaction vessel with an organic polymer material, and a method of covering only the inner surface of a glass or stainless-steel reaction vessel with an organic polymer material.

A reaction vessel may be used after washing to prevent metallic components from leaching out of an organic polymer material. Specifically, a reaction vessel is preferably washed thoroughly with an acid such as high purity nitric acid and hydrochloric acid (for example, by dipping the vessel in a solution with an acid concentration of 1 mol/L for 12 hours), and then further washed with ultrapure water or the like. In order to ensure a stable reaction, the inner surface of the reaction vessel formed of the above-described organic polymer material is preferably washed in the above-described method before reacting a quaternary alkyl ammonium hydroxide solution with chlorine gas.

In the present embodiment, as long as the surface in a reaction vessel with which a quaternary alkyl ammonium hydroxide solution is in contact is formed of an organic polymer material, the other portions may be glass, stainless steel, or passivated stainless steel. Note, however, that it is preferable that a stirring rod or the like is also formed of the same organic polymer material, which is not essential since little influence is anticipated.

In the present embodiment, when an organic solvent is used as a solvent, it is preferable to use a reaction apparatus with an explosion-proof structure. For this reason, it is preferable to use water as a solvent for a quaternary alkyl ammonium hydroxide solution in order to make the apparatus configuration simple.

(Liquid Phase of Reaction Step)

The concentration of amines contained in a liquid phase in a reaction step is preferably maintained at 100 ppm by mass or less. As described in the above-described section (Preparation Step), the inclusion of amines in a quaternary alkyl ammonium hydroxide solution causes a decrease in the concentration of hypochlorite ions produced in the reaction step.

Since hypochlorite ions generated by the reaction reacts with quaternary alkyl ammonium ions at high pH to produce tertiary amines, the amine concentration in the liquid phase increases as the reaction proceeds. In other words, the concentration of amines in the liquid phase in the reaction step tends to be higher than the concentration of amines in the preparation step. However, by maintaining the amine concentration in the liquid phase in the reaction step at 100 ppm by mass or less, decrease in the concentration of hypochlorite ions can be minimized, and a treatment liquid with high storage stability can be obtained.

(Gas Phase in Reaction Step)

The most significant feature of the present embodiment is that the concentration of carbon dioxide in the gas phase in a reaction step is 100 ppm by volume or less. In the present embodiment, a gas phase is a portion occupied by a gas in contact with a quaternary alkyl ammonium hydroxide solution in a reaction step, for example, a portion (upper space) occupied by a gas in a three-necked flask 11 in a manufacturing method shown in FIG. 1.

In the production method of the present invention, the upper limit of the carbon dioxide concentration in a gas phase is 100 ppm by volume. When the carbon dioxide concentration exceeds 100 ppm by volume, carbonate and bicarbonate ions are generated by the reactions of Formulas (1) and (2) during a reaction step, and the pH of a quaternary alkyl ammonium hypochlorite solution is lowered accordingly.

$$CO_2 + OH^- \rightarrow HCO_3^- \quad (1)$$

$$HCO_3^- + OH^- \rightarrow CO_3^{2-} + H_2O \quad (2)$$

It is speculated that when the pH is lowered by the above-described chemical reaction, the storage stability deteriorates due to decomposition of hypochlorite ions during storage of resulting quaternary alkyl ammonium hypochlorite solution.

In the production method of the present invention, when the carbon dioxide concentration in a gas phase is from 0.001 to 100 ppm by volume, preferably from 0.01 to 80 ppm by volume, the pH of a quaternary alkyl ammonium hypochlorite solution can be sufficiently controlled, and a quaternary alkyl ammonium hypochlorite solution with excellent storage stability can be produced.

In the present embodiment, it is preferable to use a quaternary alkyl ammonium hydroxide solution with a reduced amount of carbon dioxide, a chlorine gas with a reduced amount of carbon dioxide, or the like, in order to make the carbon dioxide concentration in a gas phase in the above-described range. It is preferable to carry out a reaction in the presence of an inert gas (for example, in the presence of nitrogen gas) with a reduced amount of carbon dioxide. Specifically, by using a quaternary alkyl ammonium hydroxide solution with the above-described carbon dioxide concentration and a chlorine gas with the above-described carbon dioxide concentration, and carrying out a reaction step in the presence of an inert gas, the carbon dioxide concentration in the gas phase can be set to the above-described range.

(pH of Reaction Step)

The range of pH of a liquid phase in a reaction step is 10.5 or more. Although the upper limit is not particularly limited, when the pH during a reaction is excessively high, hypochlorite ions may be decomposed and the effective chlorine concentration may be reduced when stored at the same pH for a long period of time after the reaction is completed. Therefore, the pH of the liquid phase in the reaction step is preferably less than 14, more preferably less than 13.9, and still more preferably 11 or more and less than 13.8. When the pH is in the above-described range, decomposition of hypochlorite ions is inhibited during storage of the resulting quaternary alkyl ammonium hypochlorite solution, and the storage stability is improved. Even when the pH during the reaction is high, the storage stability is improved by controlling the pH during storage to a specific range, as described below. On the other hand, when the pH of the reaction step is too low, the storage stability is reduced due to the chemical reaction represented by Formula (3).

$$2HClO + ClO^- + 2OH^- \rightarrow ClO_3^- + 2Cl^- + 2H_2O \quad (3)$$

(Reaction Temperature of Reaction Step)

The reaction temperature range of a liquid phase in a reaction step of the production method of the present invention is preferably from −35° C. to 25° C., more preferably from −15° C. to 25° C., and still more preferably from 0° C. to 25° C. When the reaction temperature is in the above-described range, a quaternary alkyl ammonium hydroxide solution and chlorine gas sufficiently react with each other to obtain a quaternary alkyl ammonium hypochlorite solution with high productivity.

When the reaction temperature is less than −35° C., a quaternary alkyl ammonium hydroxide solution begins to coagulate, and the reaction efficiency with chlorine gas tends to decrease. On the other hand, when the reaction temperature is higher than 25° C., hypochlorite ions formed in a quaternary alkyl ammonium hydroxide solution tend to decompose by heat. In particular, when the pH of a reaction is 13.8 or higher, decomposition of hypochlorite ions tends to become more noticeable at a higher reaction temperature. The reaction efficiency of quaternary alkyl ammonium hypochlorite can be evaluated as the ratio of the number of moles of hypochlorite ions produced to the number of moles of chlorine molecules supplied as raw material.

As described above, according to the production method of the present embodiment, a quaternary alkyl ammonium hypochlorite solution with excellent storage stability, such as a quaternary alkyl ammonium hypochlorite solution that retains sufficient cleaning and removal power even 10 days after production, can be produced.

As is clear from above, a quaternary alkyl ammonium hypochlorite solution obtained by the production method of the present embodiment has excellent storage stability and can be suitably used in manufacturing processes of semiconductor devices.

(Reaction Apparatus)

Figure 2:
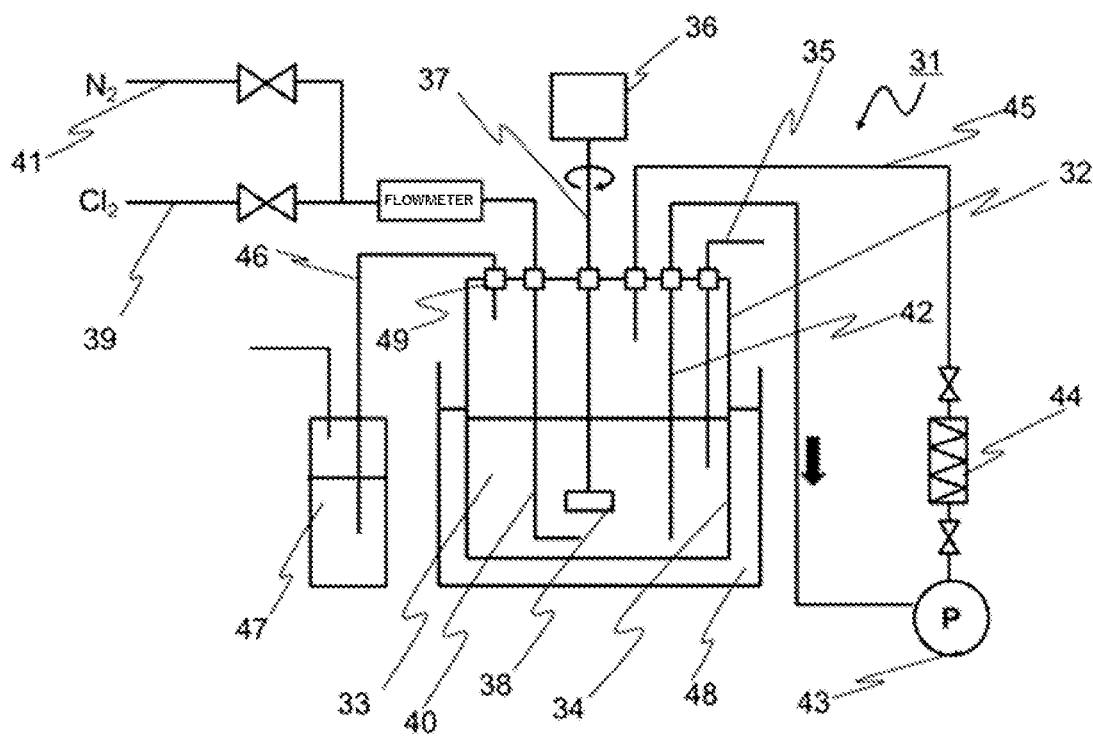
FIG. 2 is a schematic diagram illustrating a method of producing a quaternary alkyl ammonium hypochlorite solution according to a second embodiment.

Next, a reaction apparatus that can be suitably used in the production method of the present invention will be described using an example thereof. FIG. 2 illustrates a schematic view of a reaction apparatus 31.

In the reaction apparatus 31, a surface (inner surface of a reaction vessel) 34 with which a quaternary alkyl ammonium hydroxide solution 33 of the reaction vessel 32 is in contact is formed of the above-described organic polymer material. The reaction apparatus 31 can also be equipped with a thermometer (thermocouple) 35 that allows the temperature to be checked. It is also preferable to include a stirring motor 36, a stirring rod 37, and a stirring blade 38 for mixing in a reaction system. In the case of the thermometer 35, stirring rod 37, and stirring blade 38, a portion in contact with a quaternary alkyl ammonium hydroxide solution 33 is preferably formed of an organic polymer material as well.

The reaction apparatus 31 may be provided with a chlorine gas supply tube 39 that supplies chlorine gas and may be in contact with the quaternary alkyl ammonium hydroxide solution 33 via a gas introduction tube 40 that introduces chlorine gas into a reaction system through the supply tube 39. As described above, since it is preferable that the reaction system does not contain carbon dioxide, a nitrogen gas supply tube 41 can also be provided. In FIG. 2, it is configured that the nitrogen gas supply tube 41 merges with the chlorine gas supply tube 39 on the way, and that nitrogen gas is introduced from the gas introduction tube 40, but the gas introduction tube 40 may be segregated into each of the chlorine gas introduction tubes/nitrogen gas introduction tubes. Since the gas introduction tube 40 is in contact with the quaternary alkyl ammonium hydroxide solution 33, the tube is preferably formed of the above-described organic polymer material.

As will be described in detail below, in the present embodiment, when chlorine gas is contacted with a quaternary alkyl ammonium hydroxide solution to produce a quaternary alkyl ammonium hypochlorite solution, the pH in the reaction system may be lowered and solid matters including metallic components may be precipitated. In the present embodiment, a filtration system can be provided to remove or reduce such solid matters by filtration. This filtration system includes a reaction liquid transfer tube 42, a pump 43, a filtration filter 44, and a reaction liquid return tube 45. Each member in these filtration systems is preferably formed of the above-described organic polymer material because these members are in contact with a reaction solution containing a quaternary alkyl ammonium hypochlorite.

For the pump 43, a chemical diaphragm pump, a tube pump, a magnet pump, or the like can be utilized. Among them, in order to prevent contamination by metal components, it is preferable to use a pump in which a wetted part is made of the above-described fluororesin, and among them, a magnet pump is preferably used in consideration of availability.

For the filtration filters 44, those made of the material and form described in detail below are preferably used. FIG. 2 illustrates an example in which one filtration filter 44 is provided, but a plurality of filtration filters 44 can be arranged in series and/or in parallel, depending on their intended use (impurities intended to be removed).

By providing a filtration system as described above, a filtration operation can also be performed during a reaction. The supply of chlorine gas can be stopped, and after the end of the reaction, a solution containing quaternary alkyl ammonium hypochlorite can be circulated by the pump 43 to remove or reduce solid matters including metal components contained by the filtration filter 44. FIG. 2 illustrates a configuration in which a reaction apparatus and a filtration system are integrated, but a reaction apparatus and a filtration system may be provided separately as long as filtration is performed after a reaction.

A chlorine gas outlet tube 46 for releasing supplied unreacted chlorine gas and a chlorine gas trap 47 can also be provided. The chlorine gas trap 47 can be filled with, for example, about 5% by mass of sodium hydroxide aqueous solution.

A reaction bath 48 for controlling the reaction temperature can be further provided around the reaction vessel 32.

The thermometer 35, the stirring rod 37, the gas introduction tube 40, the reaction liquid transfer tube 42, the reaction liquid return tube 45, and the chlorine gas outlet tube 46 can be connected to the reaction vessel 32 by a half-joint 49 or the like.

By using the reaction apparatus 31, the method of the present embodiment can be easily carried out to produce a high purity quaternary alkyl ammonium hypochlorite solution.

(Filtration Step)

As a quaternary alkyl ammonium hydroxide solution comes into contact with chlorine gas to produce a quaternary alkyl ammonium hypochlorite solution, the pH of the solution in the reaction system decreases. In the reaction system, solid matters containing metal impurities may be precipitated. Accordingly, in order to remove or reduce these solid matters, it is preferable to further include a filtration step, in which the resulting quaternary alkyl ammonium hypochlorite solution is filtered. Further, in order to prevent decomposition of hypochlorite ions by light, the filtration step is preferably performed under shade of light. The filtration step may be performed after the storage step or dilution as described below.

In the filtration step, metal components to be filtered out may vary depending on the pH of the quaternary alkyl ammonium hypochlorite solution. Specifically, when the pH of the quaternary alkyl ammonium hypochlorite solution is 13.5 or less, preferably when the pH of the solution is more than 12.5 and 13.5 or less, hydroxides of magnesium, iron, cadmium, or the like, and oxides of nickel and silver are solidified, and therefore, these impurities can also be removed or reduced by a filtration operation.

When the pH of the quaternary alkyl ammonium hypochlorite solution is 12.5 or less, preferably when the pH of the solution is 9.0 or more and 12.5 or less, oxides of copper and lead, in addition to the above-described impurities, are solidified, and therefore these impurities can also be removed or reduced by a filtration operation. The pH of the solution may vary depending on the temperature. The above-described pH value is based on the value at 25° C. The liquid temperature for an actual filtration step is not limited to 25° C., and filtration is carried out preferably at from 20 to 28° C., and more preferably at from 23° C. to 25° C.

Such solid matters of metal impurities are formed even when the purity of raw material, quaternary alkyl ammonium hydroxide solution, and the chlorine gas, is increased. In particular, the solid matters may be formed even when the inner surface of a reaction vessel is formed of an organic polymer material. The cause of this is not clear, but it is assumed that the use of chlorine gas, a highly corrosive gas, causes metal impurities to be included in a reaction system from somewhere in a reaction apparatus.

The filtration operation can be performed at the pH at which metals to be removed or reduced are solidified. Therefore, the operation may be performed only once or a plurality of times at each pH. In such cases, a plurality of filtration filters with different pore sizes at each pH are prepared, and the filtration efficiency is improved by performing filtration in order from the filter with the largest pore size. Specifically, this can be performed by removing coarse particles in the first step and fine particles in the second step. Particles of 1 µm or more and 100 µm or less of solid matters containing metal components, such as mere metal impurities, metal oxides, metal hydroxides, and/or colloidal matters, may hereinafter be simply referred to as "coarse particles". On the other hand, particles of 0.01 µm or more and less than 1 µm may be hereinafter simply referred to as "fine particles". The particle size of solid matters refers to a circular equivalent diameter as determined by laser diffraction.

The above-described filtration operation is not particularly restricted, and can be carried out using a known filtration device and filtration filter. In order not to increase unwanted metal components, a surface with which a quaternary alkyl ammonium hypochlorite solution may come into contact in a filtration device is preferably formed of an organic polymer material. For this organic polymer, the same organic polymer can be used as the one illustrated above.

For a specific filtration filter, a filtration filter made of an organic polymeric or inorganic material is preferably used. Examples thereof include filtration filters made of polyolefin (polypropylene, polyethylene, or ultra-high molecular weight polyethylene), polysulfone, cellulose acetate, polyimide, polystyrene, the above-described fluororesin, and/or quartz fiber. It is preferable to use a combination of positively charged and negatively charged filtration filters. This is because many metal oxides and metal hydroxides are negatively charged under an alkaline atmosphere, and a positively charged filtration filter can effectively remove metal components by electrostatic adsorption. Some of metal components exist in a cationic state and are positively charged. Therefore, a negatively charged filtration filter can effectively remove ionized metal components by electrostatic adsorption.

Although the pore size of a filtration filter is not particularly restricted, a filtration filter or a microfiltration filter with a pore size of 1 μm or more, can be used for the removal of coarse particles. On the other hand, for removal of fine particles, a microfiltration filter, an ultrafiltration filter, or a nanofiltration membrane with a pore diameter of 0.01 μm or more and less than 1 μm can be used.

Commercially available filtration filters such as those described above can be used. Specifically. "Fluorogard ATX Filter (pore size: 0.05 μm)". "Quick Change ATE Filter (pore size 0.03 μm)", "Torrent ATE Filter (pore size: 0.02 μm)", "Quick Change ATE Filter (pore size: 0.03 μm)", and "FluoroLine P-1500 (pore size: 0.05 μm, 0.1 μm)" made of polytetrafluoroethylene manufactured by Entegris Japan Co., Ltd. can be used.

The above filtration operation can be carried out before adjusting the pH of a quaternary alkyl ammonium hypochlorite solution to a range suitable for the application. In this case, once the filtration operation is performed, the solution can be mixed again with chlorine gas to produce a quaternary alkyl ammonium hypochlorite solution with a desired pH. A quaternary alkyl ammonium hypochlorite solution with a desired pH can also be produced by mixing water, an acid such as hydrogen chloride, and/or an alkali such as a quaternary tetramethylammonium hydroxide solution. On the other hand, when the pH of a produced quaternary alkyl ammonium hypochlorite solution is a pH suitable for use as a cleaning liquid, the solution can be filtered and used as a cleaning liquid as it is for use in manufacturing semiconductor devices.

Such a filtration operation can particularly reduce metal components such as magnesium, iron, nickel, copper, silver, cadmium, and lead. Specifically, each content of magnesium, iron, nickel, copper, silver, cadmium, and lead can be reduced to less than 1 ppb (based on mass). The content of each of these metal components is also measured by the inductively coupled plasma mass spectrometry method shown in Examples. The form of metal components in a quaternary alkyl ammonium hypochlorite solution is not particularly limited, and may be contained as metal atoms or ions, and examples of the form also include particulates such as oxides and hydroxides, and complexes.

(Storage Step)

In the production method of the present invention, a quaternary alkyl ammonium hypochlorite solution after the above-described reaction step or after the above-described filtration step can be used as it is for a predetermined purpose, such as a cleaning liquid, and is generally used after a storage step (including storage and transportation). Quaternary alkyl ammonium hypochlorite solutions by themselves have poor storage stability, and addition of a stabilizer, for example, as described in Patent Document 4, has been required. However, a stabilizer may cause organic residue and improvement has been sought, but a quaternary alkyl ammonium hypochlorite solution obtained by the production method of the present invention is a quaternary alkyl ammonium hypochlorite solution with excellent storage stability even without addition of a stabilizer.

Furthermore, a quaternary alkyl ammonium hypochlorite solution obtained by the production method of the present invention is preferably stored by a method (storage step) of storing in which the pH of the quaternary alkyl ammonium hypochlorite solution is 12.0 or more and less than 14.0 at 25° C. and light is shaded. According to the storage step of the present invention, the oxidizing power of a quaternary alkyl ammonium hypochlorite solution during storage remains substantially unchanged, when the storage period is 30 days, preferably 60 days, and still more preferably 90 days. Therefore, after storage, a quaternary alkyl ammonium hypochlorite solution can be used for a variety of applications by simply diluting the quaternary alkyl ammonium hypochlorite solution, depending on conditions under which the solution is used. The longer the storage period, the greater the effect of improved productivity can be expected. The storage step of the present invention will be described below.

The concentration of a quaternary alkyl ammonium hypochlorite solution to be stored is not particularly restricted, and in consideration of industrial production, the solution is preferably a quaternary alkyl ammonium hypochlorite solution containing from 0.001 to 20% by mass of hypochlorite ions and from 0.001 to 50% by mass of quaternary alkyl ammonium ions at a prescribed pH. The "prescribed pH" means any pH of 12.0 or more and less than 14.0 selected as the pH in a storage step. Herein, "storage" means from the start of storage of a quaternary alkyl ammonium hypochlorite solution with a pH of 12.0 or more and less than 14.0 at 25° C. to adjustment of the concentration and/or pH of the quaternary alkyl ammonium hypochlorite solution. When the pH of a solution after adjusting the pH is 12.0 or more and to less than 14.0, a further storage of the solution still falls under the storage of the present invention. When the pH of a quaternary alkyl ammonium hypochlorite solution is 12.0 or more and less than 14.0 from the beginning, the solution can be stored as is, and when the pH is less than 12.0 or 14.0 or more, the solution can be stored after adjusting the pH to a range of 12.0 or more and less than 14.0.

When the pH in a storage step is less than 12.0, a disproportionation reaction of hypochlorite ions progresses, hypochlorite ions are decomposed, and the oxidation power of a quaternary alkyl ammonium hypochlorite solution tends to be reduced. On the other hand, when the pH is 14.0 or higher, it is presumed that organic ions, which are cations, tend to decompose. As a result, it is presumed that the disproportionate reaction of hypochlorite ions, which was inhibited by the bulkiness of organic ions, will again proceed and hypochlorite ions will decompose. A quaternary alkyl ammonium hypochlorite solution is preferably stored as a solution with a pH of 12.0 or more and less than 13.9 at 25° C., and more preferably stored as a solution with a pH of 12.0 or more and less than 13.8 at 25° C.

The pH of a solution may vary depending on the temperature. The above-described pH is based on a standard value at 25° C. The liquid temperature when a solution is actually stored is not limited to 25° C. Therefore, conditions for storage are not particularly limited, and it is preferable to store the solution under general storage conditions, specifically, from −25 to 50° C. in a known container, a canister can or a plastic storage container, and it is still more preferable to store the solution at from −20 to 40° C. in a shadable storage container, a transport container such as a canister can, or a plastic storage container filled with an inert gas in a dark place. When the temperature for storage exceeds the above-described range, the vessel may expand and be damaged by formation of oxygen molecules due to thermal decomposition of hypochlorite ions during long-term storage.

In the storage method of the present invention, the concentration of amines in a quaternary alkyl ammonium hypochlorite solution is preferably 100 ppm by mass or less. When the concentration of amines is 100 ppm by mass or less, decomposition of quaternary alkyl ammonium hypochlorite by amine is inhibited, and a quaternary alkyl ammonium hypochlorite can be stably stored.

(Dilution of Quaternary Alkyl Ammonium Hypochlorite Solution)

A quaternary alkyl ammonium hypochlorite solution may be used by appropriate dilution depending on the application. A quaternary alkyl ammonium hypochlorite solution may be diluted by any method as long as the relative concentration of hydrogen ions in the quaternary alkyl ammonium hypochlorite solution can be increased, and may be diluted with water, with a solution containing an acid, or with a solution of a pH lower than the pH of the quaternary alkyl ammonium hypochlorite solution at the time of storage. Examples of a solution with a pH lower than that of a quaternary alkyl ammonium hypochlorite solution stored using the storage method of the present invention include an alkaline solution, such as a quaternary alkyl ammonium hydroxide solution with a pH of less than 12.

The solution added to dilute a quaternary alkyl ammonium hypochlorite solution may or may not contain quaternary alkyl ammonium hypochlorite. For example, when diluting with a solution containing quaternary alkyl ammonium hypochlorite, the pH may be adjusted as well as the concentration of the quaternary alkyl ammonium hypochlorite solution may be optionally adjusted.

In the present invention, a solution added to dilute the above-described quaternary alkyl ammonium hypochlorite solution is preferably diluted with a solution whose pH is more than 0 and 7 or less. By using an acidic solution, a decrease in the concentration of quaternary alkyl ammonium hypochlorite caused by pH adjustment can be reduced. Specific examples of a solution having a pH of more than 0 and 7 or less include inorganic acids such as hydrochloric acid, nitric acid, sulfuric acid, phosphoric acid, boric acid, hydrofluoric acid, bromic acid, chloric acid, perchloric acid, iodic acid, periodic acid, and carbonic acid, and organic acids such as formic acid, acetic acid, glacial acetic acid, propionic acid, citric acid, oxalic acid, malic acid, lactic acid, and benzoic acid.

Besides, when the concentration of impurities in a solution used for dilution is high, the application of the obtained diluted solution is limited, and therefore, it is preferable that impurities in the solution used for dilution are low. For example, when a quaternary alkyl ammonium hypochlorite solution is used as a treatment liquid for semiconductor wafers, since high purity is required, it is preferable to dilute a high purity quaternary alkyl ammonium hypochlorite solution with hydrochloric acid, sulfuric acid, or the like, which is industrially easily purified.

The method of diluting a quaternary alkyl ammonium hypochlorite solution is not particularly restricted, and the solution can be diluted by any known method. For example, a quaternary alkyl ammonium hypochlorite solution and a solution used for dilution may be supplied from two supply ports of a vessel, respectively, and mixed by stirring with a propeller or a rotor, or mixed by circulating the solution with a pump. Dilution may be carried out by supplying a solution used for dilution into a vessel in which a quaternary alkyl ammonium hypochlorite solution is stored.

Another dilution method can be used in which a quaternary alkyl ammonium hypochlorite solution and a solution used for dilution are mixed at a place where a composition containing a quaternary alkyl ammonium hypochlorite solution is used to dilute the quaternary alkyl ammonium hypochlorite solution. For example, by supplying a quaternary alkyl ammonium hypochlorite solution and a solution used for dilution from two nozzles, respectively, to a use point, dilution can be carried out at the use point. This method is particularly useful when processing semiconductor wafers.

In addition, when a diluted solution is used for cleaning semiconductors, a dilution method can be employed by adding an inorganic acid or an organic acid to a quaternary alkyl ammonium hypochlorite solution. There is a method in which a tube to supply a quaternary alkyl ammonium hypochlorite solution and a tube to supply an inorganic acid or an organic acid are merged along the way for mixing to perform dilution, and the resulting diluted solution is supplied to a semiconductor wafer which is a surface to be cleaned. Known methods can be adopted for this mixing, such as: a method in which liquids are mixed by collision with each other through a narrow passage under pressure; a method in which filling materials such as glass tubes are packed into piping and repeatedly dividing, separating, and merging the flow of the liquid; and a method in which a rotatable blade powered by a motor is provided in piping.

As described above, a quaternary alkyl ammonium hypochlorite solution obtained by the production method of the present invention is stored in a storage step, and then used by diluting at the time of use, thereby making it possible to utilize a diluted solution that retains a stable oxidizing power as compared to the case of storing a quaternary alkyl ammonium hypochlorite solution at a pH of the time of use. Generally, when a quaternary alkyl ammonium hypochlorite solution is used as a cleaning liquid or the like, dilution is carried out to achieve a pH of from 8 to 12. When storing the quaternary alkyl ammonium hypochlorite solution at such a pH, the concentration of hypochlorite ions decreases and the cleaning performance is lowered. However, by going through the dilution process described above after storing the solution through the storage step described above, a diluted solution (cleaning liquid) with a high concentration of hypochlorite ions is obtained.

(Method for Processing Semiconductor Wafers)

The processing method of the present invention is a processing method capable of etching, cleaning, and removing a variety of metals and compounds thereof from a semiconductor wafer without damaging the semiconductor wafer. However, objects to be processed are not limited thereto, and, as a matter of course, the method can be used for cleaning semiconductor wafers having no metals on their surfaces, and can also be used for wet etching of metals.

The processing method of the present invention is preferably applied to a semiconductor wafer including a compound containing at least one compound selected from the group consisting of copper, tungsten, tantalum, titanium, cobalt, ruthenium, manganese, aluminum, silicon, silicon oxide, and a compound thereof. Since the present invention can effectively exert a strong oxidizing action on hypochlorite ions, the present invention can be suitably used for processing noble metals which are not easily oxidized among the above-described metals. Therefore, the processing method of the present invention can be suitably used for cleaning and removing noble metals, in particular, ruthenium. For example, when ruthenium is cleaned and removed, a known cleaning method can be employed.

(Quaternary Alkyl Ammonium Hypochlorite Solution)

Using the production method of the present invention, a quaternary alkyl ammonium hypochlorite solution with high storage stability and reduced amount of metal components can be produced without addition of stabilizers such as triazole, thiazole, tetrazole, and imidazole. Therefore, the solution can be suitably used as an etching liquid or a cleaning liquid used for manufacturing semiconductor devices. As a matter of course, solvents for a quaternary alkyl ammonium hypochlorite solution are the same as those for a quaternary alkyl ammonium hydroxide solution which is the raw material, but another solvent may be added as long as the solvent does not inhibit an effect of the present invention. However, in consideration of ease of operation, ease of handling, versatility and the like, the solvent for a quaternary alkyl ammonium hypochlorite solution is preferable to be water. The pH of the obtained quaternary alkyl ammonium hypochlorite solution is not particularly restricted, and may be determined as appropriate according to the application for which the solution is used. For example, when the pH is greater than 12.5, the solution can be used as a photoresist remover (developer), or for planarization of a noble metal layer when forming a semiconductor device.

Particularly when the pH is set to 9.0 or more and 12.5 or less, a quaternary alkyl ammonium hypochlorite solution to be obtained can also be used for etching treatment of noble metals. In this case, the pH can be set to 9.0 or more and 12.5 or less while supplying chlorine gas to a high pH quaternary alkyl ammonium hydroxide solution, which facilitates production of the solution. It is also possible to further reduce the content of metal components by additionally performing a filtration operation during or after production.

A quaternary alkyl ammonium hypochlorite solution obtained in the present invention may be substantially free of triazoles, thiazoles, tetrazoles, and imidazoles, which are described as stabilizers in Patent Document 4, and the absence thereof is preferred. Substantially free means that these stabilizers are contained at or below the detection limit in the quaternary alkyl ammonium hypochlorite solution obtained in the present invention.

In addition, a variety of other additives are optionally added to a quaternary alkyl ammonium hypochlorite solution in accordance with the application. For example, metal chelating agents, complexing agents, metal dissolution promoters, metal corrosion inhibitors, surfactants, acids, alkalis, and the like may be added as additives. By adding these additives, promotion or suppression of metal dissolution, improvement of surface roughness, improvement of processing speed, reduction of particle adhesion, and the like can be expected at the time of semiconductor wafer processing, and therefore, a cleaning liquid containing such additives can be suitably utilized for semiconductor wafer processing. As yet another additive, known additives such as benzophenones, oxanilides, and salicylates can be added to a quaternary alkyl ammonium hypochlorite solution. Addition of such additives provides favorable storage stability.

EXAMPLE

The present invention will be described in more detail by way of Examples, but the present invention is not limited to these Examples.

(pH Measurement Method)

10 mL of a treatment liquid prepared in Examples and Comparative Examples was measured for pH using a tabletop pH meter (LAQUA F-73, manufactured by HORIBA, Ltd.). The pH measurement was performed after a prepared treatment liquid was stabilized at 25° C.

(Method of Measuring Amine Concentration)

Before a preparation step, after the preparation step, during a reaction step, immediately after production, and after a storage step, 10 mL of a quaternary alkyl ammonium hydroxide solution and 10 mL of a quaternary alkyl ammonium hypochlorite solution were weighed and mixed with 10 mL of 1 mol/L sodium thiosulfate solution to deactivate hypochlorite ions in the solution. Amines in the solution were then extracted using diethyl ether and measured using a gas chromatography-mass spectrometer (Agilent 7890B/5977B, manufactured by Agilent Technology, Inc.). A calibration curve was prepared in advance using the standard addition method, and the amine concentration was quantified.

(Evaluation Method of Hypochlorite Ion Concentration)

0.5 mL of the quaternary alkyl ammonium hypochlorite solution prepared in Examples and Comparison Examples was placed in a 100 mL Erlenmeyer flask, and 2 g of potassium iodide (manufactured by FUJIFILM Wako Pure Chemical Co., Ltd., reagent special grade), 8 mL of 10% acetic acid, and 10 mL of ultrapure water were added, and stirred until solid matter was dissolved to obtain a brown solution.

The prepared brown solution was redox titrated with 0.02 M sodium thiosulfate solution (manufactured by FUJIFILM Wako Pure Chemical Co., Ltd. for volumetric analysis) until the color of the solution turned from brown to very pale yellow, and then a starch solution was added to obtain a light purple solution.

To this solution, a 0.02 M sodium thiosulfate solution was further continuously added, and at the time when the resulting solution turned to colorless and transparent, this point was regarded as end point, and an active chlorine concentration was calculated.

(Method of Calculating Reaction Efficiency)

The reaction efficiency was calculated from the ratio (%) of the number of moles of hypochlorite ions produced to the number of moles of chlorine molecules supplied. When all the added chlorine gas reacts (no decomposition occurs), the reaction efficiency is 100%. When the hypochlorite ion decomposes during the reaction, the reaction efficiency decreases.

(Method for Calculating Carbon Dioxide Concentration in Gas Phase)

The carbon dioxide concentration in a gas phase of a reaction step was measured using a $CO_2$ monitor (manufactured by CUSTOM corporation, $CO_2$-M1).

(Method for Calculating Concentration of Carbon Dioxide in Quaternary Alkyl Ammonium Hydroxide Solution)

All carbon dioxide in a quaternary alkyl ammonium hydroxide solution takes the form of carbonate ions. The concentration thereof was analyzed using an ion chromatography analyzer (DIONEX INTEGRION HPLC, manufactured by Thermo Fisher Scientific Inc.). KOH was used as an eluent, and the fluid was flowed at a flow rate of 1.2 mL/min. An anion analysis column for hydroxide eluents (AS15, manufactured by Thermo Fisher Scientific Inc.) was used as a column, and the column temperature was set at 30° C. After removing background noise by a suppressor, the carbonate ion concentration was quantified by an electrical conductivity detector, and from the result, the carbon dioxide concentration was calculated.

<Method for Evaluating Storage Stability>

A quaternary alkyl ammonium hypochlorite solution was transferred into a glove bag, and after the carbon dioxide concentration in the glove bag dropped to 1 ppm by volume or less, the solution was transferred to a PFA vessel and sealed. When stored under shade of light, the PFA vessel was covered with a clean room blackout curtain, and when not under shade of light, the PFA vessel was stored as it was. Next, after storing the vessel for 10 days in an environment of 25° C. and fluorescent lighting, the concentration of hypochlorite ions in the quaternary alkyl ammonium hypochlorite solution in the PFA vessel was measured. When the concentration ratio of hypochlorite ions (concentration after 10 days/initial concentration×100 (unit %)) was 60% or more and 100% or less, it was evaluated as "Excellent"; when the concentration ratio was 30% or more and 60% or less, it was evaluated as "Good"; and when the concentration ratio was less than 30%, it was evaluated as "Failure".

<Method of Calculating Etching Rate of Ruthenium>

An oxide film was formed on a silicon wafer using a batch thermal oxidation furnace, and 1,200 Å (±10%) of ruthenium was deposited thereon using a sputtering method. The sheet resistance was measured by a four-probe resistance meter (Lorestar-GP, manufactured by Mitsubishi Chemical Analytech Co., Ltd.) and was converted into the film thickness. 30 ml of an obtained tetramethylammonium hypochlorite solution was prepared in a beaker, and then, a tetramethylammonium hypochlorite solution whose pH was higher than 12 was diluted with an inorganic acid and an organic acid to achieve a desired pH, thereby obtaining treatment liquid. Each sample piece of ruthenium deposited wafer cut into 10×20 mm was dipped in this treatment liquid for one minute, and an etching rate was calculated as a value obtained by dividing the amount of change in film thickness before and after the treatment by the time of dipping, and evaluated as the ruthenium etching rate. However, it was known that the etching rate became slower as the pH was increased. Therefore, a practical usable range for each pH level was determined as follows. In the case of pH 9.1, a ruthenium etching rate of 300 Å/min or more was evaluated as favorable, and a rate of less than 300 Å/min was evaluated as unfavorable. In the case of pH 9.5, a ruthenium etching rate of 100 Å/min or more was evaluated as favorable, and a rate of less than 100 Å/min was evaluated as unfavorable. In the case of pH 10.5, a ruthenium etching rate of 20 Å/min or more was evaluated as favorable, and a rate of less than 20 Å/min was evaluated as unfavorable. In the case of pH 11.0, a ruthenium etching rate of 5 Å/min or more was evaluated as favorable, and a rate of less than 5 Å/min was evaluated as unfavorable.

<Method for Measuring Metal Concentration in Quaternary Alkyl Ammonium Hypochlorite Solution>

High-resolution inductively coupled plasma mass spectrometry was used to measure the metal concentration in a quaternary alkyl ammonium hypochlorite solution.

To a 25-mL perfluoroalkoxyalkane (PFA) measuring flask (manufactured by AS ONE CORPORATION, PFA measuring flask), ultrapure water and 1.25 mL of high purity nitric acid (manufactured by Kanto Chemical Co., Inc., Ultrapure-100 nitric acid) were added. Then, 0.25 mL of a quaternary alkyl ammonium hypochlorite solution was sampled using a pipette (manufactured by AS ONE CORPORATION, Pipetman P1000) and a fluororesin pipette tip (manufactured by AS ONE CORPORATION, Fluororesin pipette tip) and added to the PFA measuring flask and stirred. Next, the mixture was diluted with ultrapure water in the measuring flask to prepare a 100-fold diluted sample for measurement. Then, a high-resolution inductively coupled plasma mass spectrometer (manufactured by Thermo Fisher Scientific Inc., Element 2) was used to quantify the amount of metal by a calibration curve method. In order to confirm the increase or decrease in sensitivity due to the matrix, impurities were added to a treatment liquid to reach 2 ppb. The RF power was 1,500 W, and regarding the argon gas flow rate, the plasma gas flow rate was 15 L/min. the auxiliary gas flow rate was 1.0 L/min, and the nebulizer gas flow rate was 0.7 L/min.

Example 1

(Production of Tetramethylammonium Hypochlorite Solution)
(Preparation Step)

In a 2 L-glass four-necked flask (manufactured by Cosmos Bead Co., Ltd.), 702.2 g of a 25% by mass of a tetramethylammonium hydroxide solution and 397.8 g of ultrapure water were mixed to obtain 1,100.0 g of a 16.0% by mass of a tetramethylammonium hydroxide solution. The concentration of carbon dioxide in the solution was measured and was 1 ppm by mass or less. Furthermore, 50 g of the solution was taken out and the amine concentration was measured to be 150 ppm by mass, and therefore, amines were removed from the solution as follows. The above-described 16.0% by mass tetramethylammonium hydroxide solution prepared and a rotor (manufactured by AS ONE CORPORATION, total length 30 mm×diameter 8 mm) were put into a four-necked flask, a thermometer protection tube (manufactured by Cosmos Bead Co., Ltd., bottom-sealed type) and a thermometer were inserted through one opening, the tip of a PFA tube (manufactured by Freon Industries. Ltd., F-8011-02) connected to a chlorine gas cylinder and a nitrogen gas cylinder to allow for optional chlorine/nitrogen gas switching was dipped into the bottom of the solution through another opening, still another opening was connected to a gas washing bottle (manufactured by AS ONE CORPORATION, gas washing bottle, model number 2450/500) filled with a 5% by mass sodium hydroxide aqueous solution, and the remaining opening was connected to a syringe (manufactured by MonotaRO Co., Ltd., syringe disposal, for 10 mL) with a 5 mm diameter PTFE tube attached to a PTFE plug with a 5 mm inner diameter hole.

Next, a four-necked flask and a magnetic stirrer (manufactured by AS ONE CORPORATION, C-MAG HS10) were placed in a water bath and the stirrer was rotated and stirred at 300 rpm while heating the mixture to 40° C. Amines in the liquid were removed by flowing nitrogen gas through a PFA tube at 0.289 Pa·m$^3$/second (in terms of 0° C.) for 20 minutes, and the concentration of amines in a tetramethylammonium hydroxide solution was measured. The concentration of amines was 5 ppm by mass.

(Reaction Step)

Subsequently, the four-necked flask was covered with a clean room blackout curtain (manufactured by Tanimura Company, clean conductive PVC sheet/shading and blackout curtain TW-CPF-BK), the water bath was filled with ice water, and chlorine gas (manufactured by ADEKA Corporation, specification purity 99.999%/o, moisture content 1 ppm by volume or less) was supplied at 0.088 Pa·m$^3$/second (in terms of 0° C.) for 120 minutes while the outer periphery of the four-necked flask was cooled, and then 25 g of the treatment liquid during a reaction step was taken out of the flask using a syringe, thereby obtaining a treatment liquid during the reaction step. The concentration of carbon dioxide in a gas phase during the reaction step was 1 ppm by volume or less. Furthermore, the pH of the liquid phase during the reaction step was 14.0, and did not fall below pH 10.5 during the reaction step. Then, chlorine gas was supplied for another 120 minutes, and the reaction step was completed. The temperature was constant at 1° C. during the reaction step. The pH of a treatment liquid immediately after production was 13.8, the amine concentration was 5 ppm by mass, the hypochlorite ion concentration was 2.86% by mass, and the reaction efficiency was 99%.

(Storage Step)

After the completion of the reaction step, the treatment liquid immediately after production was transferred from a four-necked flask to a 1 L-PFA vessel, and stored at room temperature covered with a clean room blackout curtain for 10 days to obtain a treatment liquid after storage.

(Evaluation)

The pH, amine concentration, hypochlorite ion concentration and storage stability of the treatment liquid after storage for 10 days were evaluated. The results are shown in Table 2. The storage stability was evaluated in accordance with the above-described "Method for Evaluating Storage Stability", and the evaluation was "Excellent" since the concentration ratio of hypochlorite ions was 100%.

Examples 2 to 6, Comparative Examples 1 to 4

Tetramethyl ammonium hypochlorite solutions of Examples 2 to 6 were produced, stored, and evaluated in the same manner as in Example 1, except that (A) the mass concentration of tetramethyl ammonium hydroxide (TMAH) solution, (B) the pH of TMAH solution after concentration adjustment, (C) amine removal temperature, (D) nitrogen flow rate, (E) amine removal time, (F) chlorine gas supply, (G) chlorine gas flow rate, (H) temperature during reaction, (I) reaction time, (J) carbon dioxide concentration in a gas phase during a reaction step, (K) shading during reaction, and (L) shading during storage were adjusted to meet the conditions shown in Table 1. Also in Comparative Examples 1 to 4, chlorine gas was supplied without the removal of amines before the reaction. The results of the evaluation are shown in Table 2. The pH during the reaction step in Examples 2 to 7 and Comparative Examples 1 to 4 did not fall below the pH immediately after the reaction. The amine concentration during the reaction step was kept at 100 ppm or less by mass in Examples 2 to 7, and above 100 ppm by mass in Comparative Examples 1 to 4. When the amine concentration in the reaction step exceeded 100 ppm by mass, there was a decrease in reaction efficiency, whereas when the amine concentration in the reaction step was 100 ppm by mass or less, the reaction efficiency was high (95% or higher).

Example 7

The same conditions as in Example 1 were used except that a tetramethylammonium hydroxide solution with an amine concentration of 15 ppm by mass was used and no amine removal operation was performed.

In the case of low amine concentration, decomposition of hypochlorite ions generated in the reaction step was inhibited, resulting in higher reaction efficiency. Inhibition of decomposition of hypochlorite ions by amines increased the hypochlorite ion concentration ratio (concentration after 10 days/initial concentration×100 (unit %)). Shading during production and storage was found to contribute to inhibition of decomposition of hypochlorite ions.

TABLE 1

| | | | Preparation step | | | | |
|---|---|---|---|---|---|---|---|
| | 25% TMAH [g] | Ultrapure water [g] | (A) TMAH concentration [% by mass] | (B) pH immediately after preparation | (C) Amine removal temperature [° C.] | (D) Nitrogen flow rate [Pa · m³/sec] | (E) Amine removal time [min] |
| Example 1 | 702.2 | 397.8 | 16.0 | 14.2 | 40 | 0.289 | 20 |
| Example 2 | 702.2 | 397.8 | 16.0 | 14.2 | 25 | 0.289 | 20 |
| Example 3 | 702.2 | 397.8 | 16.0 | 14.2 | 40 | 0.289 | 20 |
| Example 4 | 609 | 491 | 13.8 | 14.2 | 40 | 0.289 | 20 |
| Example 5 | 702.2 | 397.8 | 15.0 | 14.2 | 40 | 0.289 | 20 |
| Example 6 | 702.2 | 397.8 | 15.0 | 14.2 | 40 | 0.289 | 20 |
| Example 7 | 702.2 | 397.8 | 16.0 | 14.2 | — | — | — |
| Comparatve Example 1 | 702.2 | 397.8 | 16.0 | 14.2 | — | — | — |
| Comparatve Example 2 | 702.2 | 397.8 | 16.0 | 14.2 | — | — | — |
| Comparatve Example 3 | 702.2 | 397.8 | 15.0 | 14.2 | — | — | — |
| Comparatve Example 4 | 702.2 | 397.8 | 16.0 | 14.2 | — | — | — |

| | | | Reaction step | | | | Storage step |
|---|---|---|---|---|---|---|---|
| | (F) Cl₂ supply [mL] | (G) Cl₂ flow rate [Pa · m³/sec] | (H) Temperature during reaction [° C.] | (I) Reaction time [min] | (J) CO₂ concentration in gas phase during reaction step | (K) Shading during reaction | (L) Shading during storage |
| Example 1 | 12,552 | 0.088 | 11 | 240 | <1 ppm | Yes | Yes |
| Example 2 | 12,552 | 0.088 | 11 | 240 | <1 ppm | Yes | Yes |
| Example 3 | 12,552 | 0.088 | 11 | 240 | <1 ppm | No | Yes |
| Example 4 | 12,552 | 0.088 | 11 | 240 | <1 ppm | Yes | No |
| Example 5 | 12,552 | 0.088 | 11 | 240 | <1 ppm | Yes | No |
| Example 6 | 12,552 | 0.088 | 11 | 240 | <1 ppm | No | No |
| Example 7 | 12,552 | 0.088 | 11 | 240 | <1 ppm | Yes | Yes |
| Comparatve Example 1 | 12,552 | 0.088 | 11 | 240 | <1 ppm | Yes | Yes |
| Comparatve Example 2 | 12,552 | 0.088 | 11 | 240 | <1 ppm | Yes | No |

TABLE 1-continued

| | | | | | | | |
|---|---|---|---|---|---|---|---|
| Comparatve Example 3 | 12,552 | 0.088 | 11 | 240 | <1 ppm | No | Yes |
| Comparatve Example 4 | 12,552 | 0.088 | 11 | 240 | <1 ppm | No | No |

| | Carbon dioxide concentration in TMAH [ppm by mass] | pH | | | Amine concentration [ppm by mass] | | |
|---|---|---|---|---|---|---|---|
| | | During reaction step | Immediately after production | After 10 days | Before preparation step | After preparation step | During reaction step |
| Example 1 | <1 | 14 | 13.8 | 13.8 | 150 | 5 | 5 |
| Example 2 | <1 | 14 | 13.8 | 13.8 | 150 | 15 | 15 |
| Example 3 | <1 | 14 | 13.8 | 13.8 | 152 | 5 | 20 |
| Example 4 | <1 | 14 | 13.6 | 13.8 | 150 | 5 | 5 |
| Example 5 | <1 | 14 | 13.8 | 13.8 | 150 | 5 | 5 |
| Example 6 | <1 | 14 | 13.8 | 13.8 | 150 | 5 | 18 |
| Example 7 | <1 | 14 | 13.8 | 13.8 | 15 | 15 | 15 |
| Comparative Example 1 | <1 | 14 | 13.8 | 13.8 | 200 | 200 | 202 |
| Comparatve Example 2 | <1 | 14 | 13.8 | 13.8 | 150 | 150 | 150 |
| Comparative Example 3 | <1 | 14 | 13.8 | 13.8 | 152 | 152 | 170 |
| Comparative Example 4 | <1 | 14 | 13.8 | 13.8 | 160 | 160 | 173 |

| | Amine concentration [ppm by mass] | | Hypochlorite ion concentration [%] | | | Reaction efficiency [%] | Storage stability |
|---|---|---|---|---|---|---|---|
| | Immediately after production | After 10 days | Calculated value | Immediately after production | After 10 days | | |
| Example 1 | 5 | 5 | 2.88 | 2.86 | 2.86 | 99 | Excellent |
| Example 2 | 15 | 20 | 2.88 | 2.75 | 2.68 | 95 | Excellent |
| Example 3 | 29 | 51 | 2.88 | 2.83 | 2.55 | 98 | Excellent |
| Example 4 | 5 | 129 | 2.88 | 2.86 | 1.63 | 99 | Good |
| Example 5 | 5 | 810 | 2.88 | 2.86 | 1.10 | 97 | Good |
| Example 6 | 24 | 955 | 2.88 | 2.83 | 0.91 | 98 | Good |
| Example 7 | 15 | 15 | 2.88 | 2.86 | 2.86 | 99 | Excellent |
| Comparative Example 1 | 206 | 300 | 2.88 | 2.60 | 1.22 | 90 | Good |
| Comparatve Example 2 | 151 | 1289 | 2.88 | 2.66 | 0.42 | 92 | Failure |
| Comparative Example 3 | 184 | 242 | 2.88 | 2.53 | 1.31 | 89 | Good |
| Comparative Example 4 | 189 | 1005 | 2.88 | 2.51 | 0.71 | 87 | Failure |

Example 8

<Production of Tetramethylammonium Hypochlorite Solution>

253 g of a 25% by mass tetramethylammonium hydroxide (TMAH) aqueous solution with a $CO_2$ content of 2 ppm by mass and an amine concentration of 5 ppm by mass or less and 747 g of ion exchange water were mixed in a 2 L-glass four-necked flask (manufactured by Cosmos Bead Co., Ltd.) to obtain a 6.3% by mass TMAH solution with a $CO_2$ content of 0.5 ppm by mass. The pH of the solution was 13.8. The $CO_2$ concentration in the laboratory was 350 ppm by volume.

Next, as shown in FIG. 1, using the same method as in Example 1, a rotor 14 (manufactured by AS ONE CORPORATION, total length 30 mm×diameter 8 mm) were put into a four-necked flask 11, a thermometer protection tube 12 (manufactured by Cosmos Bead Co., Ltd., bottom-sealed type) and a thermocouple 13 were inserted through one opening, the tip of a PFA tube 15 (manufactured by Freon Industries, Ltd., F-8011-02) connected to a chlorine gas cylinder and a nitrogen gas cylinder to allow for optional chlorine/nitrogen gas switching was dipped into the bottom of the solution through another opening, another opening was connected to a gas washing bottle 16 (manufactured by AS ONE CORPORATION, gas washing bottle, model number 2450/500) filled with a 5% by mass sodium hydroxide aqueous solution 17, and the remaining opening was connected to a syringe (manufactured by MonotaRO Co., Ltd., syringe disposal, for 10 mL) with a 5 mm diameter PTFE tube attached to a PTFE plug with a 5 mm inner diameter hole.

Next, a four-necked flask and a magnetic stirrer (manufactured by AS ONE CORPORATION, C-MAG HS10) were placed in a water bath, and while rotating and stirring at 300 rpm, $CO_2$ in a gas phase was removed by flowing nitrogen gas through a PFA tube at 0.289 Pa·m$^3$/second (in terms of 0° C.) for 20 minutes. The $CO_2$ concentration in the gas phase of the flask was 1 ppm by volume or less. Subsequently, the four-necked flask was covered with a clean room blackout curtain (manufactured by Tanimura Company, clean conductive PVC sheet/shading and blackout curtain TW-CPF-BK), the water bath was filled with ice water, and chlorine gas (manufactured by ADEKA Corporation, specification purity 99.999%, moisture content 1 ppm by volume or less) was supplied at 0.088 Pa·m³/second (in terms of 0° C.) for 90 minutes while the outer periphery of the four-necked flask was cooled, and then 25 g of the treatment liquid during a reaction step was taken out of the flask using a syringe, thereby obtaining a treatment liquid during the reaction step. Then, chlorine gas was supplied for another 90 minutes, and the reaction step was completed. The liquid temperature was 11° C. during the reaction step. After the completion of the reaction step, 25 g of the treatment liquid was taken out of the four-necked flask as a treatment liquid immediately after production. The four-necked flask with the treatment liquid was placed in a glove bag with a carbon dioxide concentration of 1 ppm or less without any contact with the atmosphere. Thereafter, the treatment liquid immediately after production was transferred from a four-necked flask to a 1 L-PFA vessel, and stored at room temperature covered with a clean room blackout curtain for 10 days to obtain a treatment liquid after storage.

<Evaluation>

Comparing the concentration of hypochlorite ions and the pH before and after storage for 10 days, it was found that the evaluation result of storage stability was "Excellent".

Examples 9 to 14

Tetramethylammonium hypochlorite solutions of Examples 9 to 14 were prepared and evaluated in the same manner as in Example 8, except that (A) the mass concentration of the TMAH solution, (B) the pH of the TMAH solution, (F) the chlorine gas supply, (G) the supply rate, (H) the reaction temperature, and (J) the carbon dioxide concentration in the gas phase were adjusted to meet the conditions shown in Table 3. In Example 14, the reaction step was not cooled, and the reaction temperature was increased from 25° C. to 35° C. A tetramethylammonium hydroxide solution with an amine concentration of 20 ppm by mass or less was used.

Comparative Example 5

Figure 3:
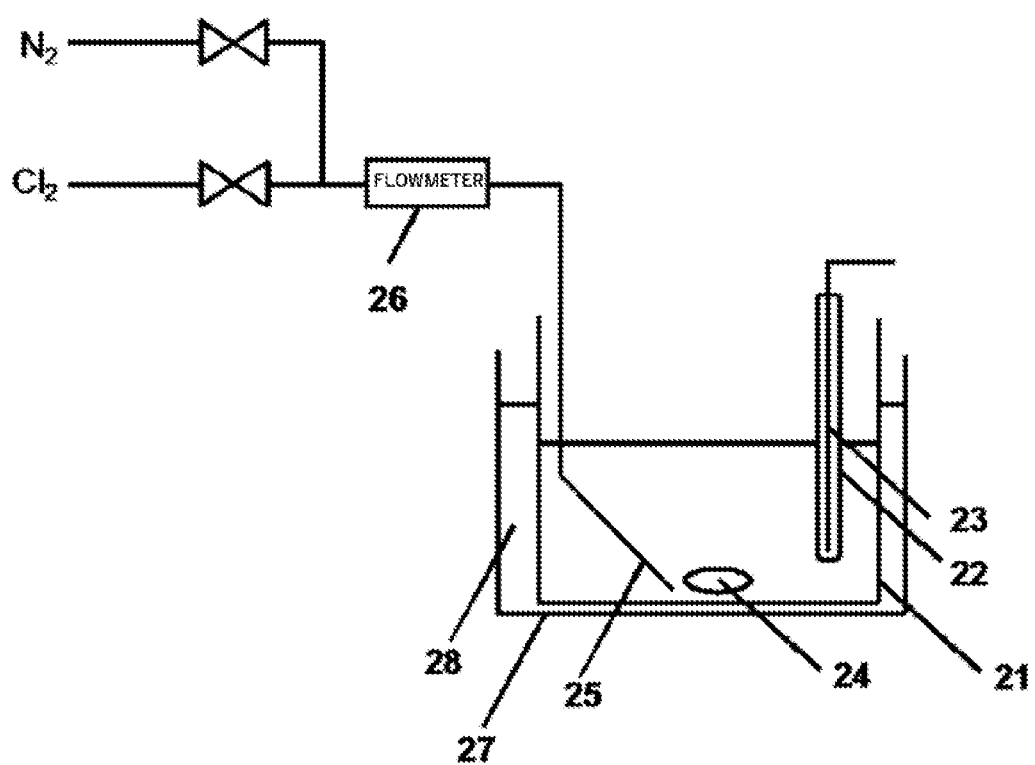
FIG. 3 is a schematic diagram illustrating one aspect of a general production method of a quaternary alkyl ammonium hypochlorite solution.

In a 2 L-glass beaker (manufactured by AS ONE CORPORATION), 233 g of a 25% by mass TMAH solution with a $CO_2$ content of 2 ppm by mass and 767 g of ion exchange water were mixed to obtain a 5.8% by mass TMAH solution. The pH of the solution was 13.8. Next, as shown in FIG. 3, a rotor 24 (manufactured by AS ONE CORPORATION, length 30 mm×diameter 8 mm) was placed in a glass beaker 21, then, a thermometer protection tube 22 (manufactured by Cosmos Bead Co., Ltd., bottom-sealed type) and a thermocouple 23 were inserted, and the tip of a PFA tube 25 (manufactured by Freon Industries, Ltd., F-8011-02) connected to a chlorine gas cylinder was dipped into the bottom of the solution. The carbon dioxide concentration in the gas phase was 350 ppm by volume.

Subsequently, a magnetic stirrer (manufactured by AS ONE CORPORATION, C-MAG HS10) was placed at the bottom of the glass beaker and rotated at 300 rpm while the outer periphery of the glass beaker was cooled with ice water 28, and chlorine gas (manufactured by ADEKA CORPORATION, specification purity 99.999%, moisture content 1 ppm by volume or less) was supplied at 0.064 Pa·m³/second (in terms of 0° C.) for 180 minutes to obtain a tetramethylammonium hypochlorite solution. The temperature of the solution during the reaction was 11° C.

The obtained solution was placed in a glove bag with a carbon dioxide concentration of 1 ppm by volume or less to avoid contact with the atmosphere, transferred to a 1 L-PFA vessel, covered with a clean room blackout curtain, and stored at room temperature for 10 days to obtain a treatment liquid after storage. Comparing the concentration of hypochlorite ions and the pH before and after storage for 10 days, the storage stability was evaluated.

Comparative Examples 6 and 7

The tetramethylammonium hypochlorite solutions of Comparative Examples 6 and 7 were prepared and evaluated in the same manner as in Comparative Example 5, except that (A) the mass concentration of tetramethylammonium hydroxide solution, (B) the pH of tetramethylammonium hydroxide solution, (F) the chlorine gas supply, (G) the supply rate, (H) the reaction temperature, and (J) the carbon dioxide concentration in the gas phase were adjusted to meet the conditions shown in Table 3. However, in Comparative Example 7, a solution with a carbon dioxide concentration of 771 ppm by mass in a tetramethylammonium hydroxide solution was used.

The evaluation results are shown in Table 4. By removing carbon dioxide, the pH in the reaction step was kept at 10.5 or higher, and a chemical solution with excellent storage stability was obtained.

TABLE 3

|  | Preparation step | | | | Reaction step | | | | (J) $CO_2$ concentration in gas phase during reaction step [ppm by volume] |
|---|---|---|---|---|---|---|---|---|---|
|  | 25% TMAH [g] | Ion exchange water [g] | (A) TMAH concentration [% by mass] | (B) pH immediately after preparation | (F) $Cl_2$ supply [mL] | (G) $Cl_2$ flow rate [Pa·m³/sec] | (H) Temperature during reaction [° C.] | (I) Reaction time [min] | |
| Example 8 | 253 | 747 | 6.3 | 13.8 | 6,810 | 0.064 | 11 | 180 | <1 |
| Example 9 | 233 | 767 | 5.8 | 13.8 | 6,810 | 0.064 | 11 | 180 | <1 |
| Example 10 | 339 | 661 | 8.5 | 14.0 | 9,478 | 0.089 | 5 | 180 | <1 |
| Example 11 | 339 | 661 | 8.5 | 14.0 | 9,478 | 0.089 | 15 | 180 | <1 |
| Example 12 | 253 | 747 | 6.3 | 13.8 | 6,810 | 0.064 | 11 | 180 | 50 |
| Example 13 | 339 | 661 | 8.5 | 14.0 | 9,478 | 0.089 | 25 | 180 | <1 |
| Example 14 | 339 | 661 | 8.5 | 14.0 | 9,478 | 0.089 | 25 -> 35 (Without cooling) | 180 | <1 |

TABLE 3-continued

| | Preparation step | | | | Reaction step | | | | |
|---|---|---|---|---|---|---|---|---|---|
| | 25% TMAH [g] | Ion exchange water [g] | (A) TMAH concentration [% by mass] | (B) pH immediately after preparation | (F) Cl$_2$ supply [mL] | (G) Cl$_2$ flow rate [Pa · m$^3$/sec] | (H) Temperature during reaction [° C.] | (I) Reaction time [min] | (J) CO$_2$ concentration in gas phase during reaction step [ppm by volume] |
| Comparatve Example 5 | 233 | 767 | 5.8 | 13.8 | 6,810 | 0.064 | 11 | 180 | 350 |
| Comparatve Example 6 | 192 | 808 | 4.8 | 13.7 | 5,892 | 0.055 | 11 | 180 | 350 |
| Comparatve Example 7 | 233 | 767 | 5.8 | 13.8 | 6,810 | 0.064 | 11 | 180 | 350 |

TABLE 4

| | Carbon dioxide concentration in TMAH [ppm by mass] | Amine concentration [ppm by mass] | | pH | | | Hypochlorite ion concentration [% by mass] | | Storage stability |
|---|---|---|---|---|---|---|---|---|---|
| | | After preparation step | During reaction step | After preparation step | Immediately after production | After 10 days | Immediately after production | After 10 days | |
| Example 8 | <1 | 5 | 5 | 13.8 | 13.0 | 13.0 | 1.59 | 1.59 | Excellent |
| Example 9 | <1 | 7 | 7 | 13.8 | 12.0 | 12.0 | 1.59 | 1.59 | Excellent |
| Example 10 | <1 | 5 | 5 | 14.0 | 13.0 | 13.0 | 2.19 | 2.19 | Excellent |
| Example 11 | <1 | 6 | 6 | 14.0 | 13.0 | 13.0 | 2.19 | 2.19 | Excellent |
| Example 12 | <1 | 5 | 7 | 13.8 | 12.5 | 12.5 | 1.59 | 1.59 | Excellent |
| Example 13 | <1 | 5 | 5 | 14.0 | 13.0 | 13.0 | 2.08 | 2.08 | Excellent |
| Example 14 | <1 | 5 | 5 | 14.0 | 13.0 | 13.0 | 1.27 | 1.27 | Excellent |
| Comparatve Example 5 | <1 | 8 | 8 | 13.8 | 9.2 | 9.0 | 1.55 | 0.74 | Good |
| Comparatve Example 6 | <1 | 7 | 7 | 13.7 | 9.4 | 9.2 | 1.36 | 0.78 | Good |
| Comparatve Example 7 | 771 | 7 | 7 | 13.8 | 9.1 | 8.9 | 1.50 | 0.66 | Good |

Example 15

<Production of Tetramethylanmmonium Hypochlorite Solution>
(Preparation Step)

As shown in FIG. 2, a reaction vessel 32 processed to allow a plurality of Polytetrafluoroethylene Half Joints 49 (manufactured by AS ONE CORPORATION, Half Female Joint I Type 6φ) to be connected to 2 L-capacity polytetrafluoroethylene reaction vessel (manufactured by AS ONE CORPORATION, 2000 cc cylindrical reaction vessel type C). 253 g of 25% by mass tetramethylammonium hydroxide solution and 747 g of ultrapure water were mixed into the reaction vessel 32 to obtain a tetramethylammonium hydroxide solution of 6.3% by mass, 5 ppm by mass CO$_2$ content, and pH 13.8 (25° C.). Each the contents of sodium, potassium, aluminum, magnesium, iron, nickel, copper, silver, cadmium, and lead in this tetramethylammonium hydroxide solution was less than 1 ppb, and the amine concentration was 5 ppm by mass.
(Reaction Step)

A stirring rod 37 (manufactured by AS ONE CORPORATION, made of polytetrafluoroethylene (PTFE), with stirring rod and stirring blades, length 450 mm×8 mm diameter) was placed in the center of the reaction vessel 32 and an upper portion was fixed with a stirring motor 36 (Shinto Scientific Co., Ltd., Three-One Motor BLh600). A thermometer 35 was set in the reaction vessel 32 to allow monitoring of the temperature during a reaction.

The tip of a gas introduction tube 40 (manufactured by Freon Industries. Inc., PFA tube) made of tetrafluoroethylene-perfluoroalkyl vinyl ether copolymer, which was set to allow switching between chlorine gas (chlorine gas introduction tube 39)/nitrogen gas (nitrogen gas supply tube 41), was dipped into the bottom of the solution (tetramethylammonium hydroxide solution 33).

One half-joint was connected to a chlorine gas trap 47 (manufactured by AS ONE CORPORATION, a gas washing bottle) filled with a 5% by mass sodium hydroxide aqueous solution via a chlorine gas discharge tube 46.

One half-joint and the inlet side of a magnetic pump 43 (manufactured by AS ONE CORPORATION, Teflon (registered trademark) surface coated magnetic pump) were connected with a reaction liquid transfer tube 42, a tube made of a tetrafluoroethylene perfluoroalkyl vinyl ether copolymer (manufactured by Freon Industries, Inc., PFA tube), and then, the outlet side was connected with a filtration filter 44 (manufactured by Integris Japan, Fluorogard AT, pore size 0.1 µm) and a reaction liquid return tube 45 made of the same material as the reaction liquid transfer tube 42.

One half-joint was connected to a syringe (manufactured by MonotaRO Co., Ltd., syringe disposal, for 10 mL) with a 6 mm outer diameter PTFE tube attached, and the tube tip was adjusted to be positioned at the bottom of the reaction vessel 32.

Next, nitrogen gas with a carbon dioxide concentration of less than 1 ppm by volume was flowed through the nitrogen gas supply tube 41, a gas supply tube 40 (tetrafluoroethylene perfluoroalkyl vinyl ether copolymer tube (manufactured by Freon Industries, Inc., PFA tube)) for 20 minutes at 0.29 Pa·m$^3$/sec to purge carbon dioxide in the gas phase in the reaction vessel 32.

Subsequently, the stirring motor 36 was rotated at 300 rpm, and chlorine gas (manufactured by ADEKA Corporation, specification purity 99.999%, moisture content 1 ppm by volume or less) was supplied at 0.064 Pa·m$^3$/sec while cooling the periphery of the reaction vessel 32 with a reaction bath 48 (ice water). The carbon dioxide concentration in the gas phase during the reaction step was 1 ppm by volume or less. During the reaction with chlorine gas supply, the pump 43 was activated to produce a tetramethylammonium hypochlorite solution while performing a filtration operation (the filtration operation was performed even when the pH of the reaction solution was higher than 13.5° C. (25° C.)). After supplying chlorine gas for 90 minutes, 25 g of the solution was taken out using a syringe to obtain a treatment liquid during the reaction step. The pH of the liquid phase during the reaction step was 13.4, and did not fall below pH 10.5 during the reaction step. The reaction step was then completed by supplying gas for another 90 minutes. The temperature was kept constant at 11° C. during the reaction step. Immediately after production (at the end of the reaction step), the pH of the treatment liquid was 13.0, the amine concentration was 5 ppb by mass or less, the hypochlorite ion concentration was 1.59% by mass, and the metal content was less than 1 ppb by mass in all cases.

(Storage Step)

The obtained solution was transferred to a 1 L-PFA vessel in a glove bag with a carbon dioxide concentration of 1 ppm by volume or less to avoid contact with the atmosphere, covered with a clean room blackout curtain, and stored at room temperature for 10 days to obtain a treatment liquid after storage. Comparing the concentration of hypochlorite ions and the pH before and after storage for 10 days, the storage stability was evaluated.

(Evaluation)

The pH, the amine concentration, the hypochlorite ion concentration, and the storage stability of the treatment liquid after 10 days of storage were evaluated. The results are shown in Table 6. Since the concentration ratio of hypochlorite ions was 100%, the storage stability was "Excellent".

Examples 16 to 18

Tetramethylammonium hypochlorite solutions of Examples 16 to 18 were prepared in the same manner as in Example 15, except that (A) the mass concentration of TMAH aqueous solution (one containing less than 1 ppb by mass of sodium, potassium, aluminum, magnesium, iron, nickel, copper, silver, cadmium, and lead, with a carbon dioxide concentration of 2 ppm by mass was used) was adjusted to meet the conditions shown in Table 5, and the metal content of the solutions was examined.

However, in Example 16, after supplying total chlorine gas, the pump 43 was activated, and a filtration operation was performed for 180 minutes after stopping the chlorine gas supply. The pH at the end of the total chlorine gas supply was 12.0, and the pH after filtration was 12.0. In Example 17, the filtration operation was not performed. In Example 18, the filtration operation was performed when the pH of the treatment liquid was from 13.8 to 13.6. The results are shown in Table 6.

Examples 19 and 20 and Comparative Example 8

A tetramethylammonium hypochlorite solution was produced under the conditions shown in Table 5, except that a 1,000-mL glass reaction vessel (manufactured by SIBATA SCIENTIFIC TECHNOLOGY LTD., 1 L-separable reaction vessel) with a glass side tube of 19/38 mm sliding size was used as the reaction vessel 32. The results are shown in Table 6.

However, in Example 19, the filtration operation was performed by starting the pump 43 while the chlorine gas was being supplied. In Example 20, the filtration operation was not performed. In Comparative Example 8, after supplying all chlorine gas, the pump 43 was activated and the filtration operation was carried out for 180 minutes after stopping the supply of chlorine gas. The results are shown in Table 6.

When a polytetrafluoroethylene reaction vessel was used, the concentration of metal impurities such as sodium, potassium, and aluminum could be reduced because elution from the reaction vessel could be controlled. Magnesium, iron, nickel, copper, silver, cadmium, and lead were found to be removed by filtration of tetramethylammonium hypochlorite solution at pH 13.5 or lower during the reaction step or immediately after reaction.

TABLE 5

| | (A) TMAH concentration [% by mass] | (B) pH immediately after preparation | (F) Cl$_2$ supply [mL] | (G) Cl$_2$ flow rate [Pa · m$^3$/sec] | (H) Temperature during reaction [° C.] | (I) Reaction time [min] | (J) CO$_2$ concentration in gas phase during reaction step | (M) Reaction vessel | (N) Filtration |
|---|---|---|---|---|---|---|---|---|---|
| Example 15 | 6.3 | 13.8 | 6810 | 0.064 | 11 | 180 | <1 ppm | PTFE | During reaction |
| Example 16 | 5.8 | 13.8 | 6810 | 0.064 | 11 | 180 | <1 ppm | PTFE | After reaction |
| Example 17 | 5.8 | 13.8 | 6810 | 0.064 | 11 | 180 | <1 ppm | PTFE | No |
| Example 18 | 6.3 | 13.8 | 6810 | 0.064 | 11 | 180 | <1 ppm | PTFE | During reaction |
| Example 19 | 6.3 | 13.8 | 6810 | 0.064 | 11 | 180 | <1 ppm | glass | During reaction |
| Example 20 | 5.8 | 13.8 | 6810 | 0.064 | 11 | 180 | <1 ppm | glass | No |
| Comparatve Example 8 | 4.8 | 13.7 | 5892 | 0.055 | 11 | 180 | <1 ppm | glass | After reaction |

TABLE 6

| | Carbon dioxide concentration in TMAH [ppm by mass] | Amine concentration [ppm by mass] | | pH | | | Hypochlorite ion concentration (% by mass) | | Storage stability |
|---|---|---|---|---|---|---|---|---|---|
| | | During Preparation step | During reaction step | During reaction step | Immediately after production | After 10 days | Immediately after production | After 10 days | |
| Example 15 | <1 | 5 | 5 | 13.4 | 13.0 | 13.0 | 1.59 | 1.59 | Excellent |
| Example 16 | <1 | 5 | 5 | 12.9 | 12.0 | 12.0 | 1.59 | 1.59 | Excellent |
| Example 17 | <1 | 5 | 5 | 12.9 | 12.0 | 12.0 | 1.59 | 1.59 | Excellent |
| Example 18 | <1 | 5 | 5 | 13.4 | 13.0 | 13.0 | 1.59 | 1.59 | Excellent |
| Example 19 | <1 | 5 | 5 | 13.4 | 13.0 | 13.0 | 1.59 | 1.59 | Excellent |
| Example 20 | <1 | 5 | 5 | 12.9 | 12.0 | 12.0 | 1.59 | 1.59 | Excellent |
| Comparative Example 8 | <1 | 6 | 6 | 12.0 | 10.2 | 10.2 | 1.36 | 0.76 | Good |

| | Metal impurities concentration (ppb by mass) | | | | | | | | | |
|---|---|---|---|---|---|---|---|---|---|---|
| | Na | K | Al | Mg | Fe | Ni | Cu | Ag | Cd | Pb |
| Example 15 | <1 | <1 | <1 | <1 | <1 | <1 | <1 | <1 | <1 | 4 |
| Example 16 | <1 | <1 | <1 | <1 | <1 | <1 | <1 | <1 | <1 | 4 |
| Example 17 | <1 | <1 | <1 | 13 | 6 | 10 | 3 | 3 | 3 | 3 |
| Example 18 | <1 | <1 | <1 | 15 | 6 | 9 | 3 | 4 | 3 | 3 |
| Example 19 | 210 | 25 | 49 | <1 | <1 | <1 | <1 | <1 | <1 | <1 |
| Example 20 | 220 | 24 | 55 | 20 | 9 | 11 | 3 | 3 | 3 | 3 |
| Comparative Example 8 | 105 | 16 | 30 | <1 | <1 | <1 | <1 | <1 | <1 | <1 |

Example 21

100 mL of the tetramethylammonium hypochlorite solution obtained in Example 8 was placed in a PFA vessel, shaded from light, and stored in an environment at 25° C. for 30 days. The pH of the tetramethylammonium hypochlorite solution was 13.0 after 30 days of storage. Since the concentration ratio of hypochlorite ions was 100% immediately after production and after 30 days of storage, the storage stability was "Excellent". The amine concentration was 5 ppm by mass or less. To the tetramethylammonium hypochlorite solution after 30 days of storage, 8.8 mL of 35.0% by mass high-purity hydrochloric acid was added to dilute the pH (25° C.) to 9.5 (prepared in a PFA vessel). The tetramethylammonium hypochlorite solution obtained by dilution contained less than 1 ppb of sodium, potassium, aluminum, magnesium, iron, nickel, copper, silver, cadmium, and lead, respectively.

30 mL of tetramethylammonium hypochlorite solution with pH 9.5, obtained by dilution, was placed in a beaker (PFA beaker), and the etching rate of ruthenium was evaluated according to the "Method of Calculating Etching Rate of Ruthenium" above, with the result that the etching rate was 345 Å/min, which was favorable.

Examples 22 to 28 and Comparative Example 9

Tetramethylammonium hypochlorite solutions of Examples 22 to 28 and Comparative Example 9 were prepared and evaluated in the same manner as in Example 8, except that (A) the mass concentration of tetramethylammonium hydroxide (TMAH) solution. (B) the pH after preparation, (F) the chlorine gas supply, (G) the chlorine gas flow rate, (H) the reaction temperature, (O) the diluent solution, (P) the concentration of diluent solution, and (Q) the amount of diluent solution were changed to meet the conditions shown in Table 7. Since the tetramethylammonium hypochlorite solution obtained in Example 28 immediately after production had a pH of 14.0 or higher, the solution was stored for 30 days after addition of 35.0% by mass of high-purity hydrochloric acid until the pH reached 13.0. Since the tetramethylammonium hypochlorite solution obtained in Comparative Example 9 had a pH of 10 or less after 30 days of storage, dilution of the tetramethylammonium hypochlorite solution was not carried out. The results are shown in Table 8.

It was found that when a tetramethylammonium hypochlorite solution was stored at the pH of less than 12.0 or at the pH of 14.0 or more, decomposition of hypochlorite ions was accelerated and the storage stability was deteriorated. It was found that the amine concentration tended to increase during storage particularly at the pH of 14.0 or higher, which accelerated decomposition of hypochlorite ions. Therefore, when the pH of the tetramethylammonium hypochlorite solution immediately after production was 14.0 or more, the increase in the amine concentration during storage was suppressed by preparation with the pH of less than 14.0, which suppressed decomposition of hypochlorite ions and resulted in favorable storage stability. As a result, it was found that a stable Ru etching rate was obtained.

TABLE 7

| | Preparation step | | | (B) pH | Reaction step | |
|---|---|---|---|---|---|---|
| | 25% TMAH [g] | Ion exchange water [g] | (A) TMAH concentration [% by mass] | immediately after preparation | (F) $Cl_2$ supply [mL] | (G) $Cl_2$ flow rate [Pa · m³/sec] |
| Example 21 | 253 | 747 | 6.3 | 13.8 | 6810 | 0.064 |
| Example 22 | 244 | 756 | 6.1 | 13.8 | 6610 | 0.064 |
| Example 23 | 264 | 736 | 6.6 | 13.9 | 6810 | 0.064 |
| Example 24 | 253 | 747 | 6.3 | 13.8 | 6810 | 0.064 |
| Example 25 | 253 | 747 | 6.3 | 13.8 | 6810 | 0.064 |
| Example 26 | 253 | 747 | 6.3 | 13.8 | 6610 | 0.064 |
| Example 27 | 253 | 747 | 6.3 | 13.8 | 6810 | 0.064 |
| Example 28 | 640 | 360 | 16.0 | 14.2 | 6810 | 0.064 |
| Comparatve Example 9 | 233 | 767 | 5.8 | 13.8 | 6810 | 0.064 |

| | Reaction step | | | During use | | |
|---|---|---|---|---|---|---|
| | (H) Temperature during reaction [° C.] | (I) Reaction time [min] | (J) $CO_2$ concentration of gas phase during reaction step [ppm by volume] | (O) Diluent solution | (P) Diluent solution concentration [%] | (Q) Amount of diluent solution added [mL] |
| Example 21 | 11 | 180 | <1 | Hydrochloric acid | 35.0 | 8.8 |
| Example 22 | 11 | 180 | <1 | Hydrochloric acid | 35.0 | 2.8 |
| Example 23 | 11 | 180 | <1 | Hydrochloric acid | 35.0 | 28.0 |
| Example 24 | 11 | 180 | <1 | Nitric acid | 70.0 | 10.0 |
| Example 25 | 11 | 180 | <1 | Acetic acid | 100.0 | 5.7 |
| Example 26 | 11 | 180 | <1 | Hydrochloric acid | 35.0 | 8.5 |
| Example 27 | 11 | 180 | <1 | Hydrochloric acid | 35.0 | 8.7 |
| Example 28 | 11 | 180 | <1 | Hydrochloric acid | 35.0 | 8.8 |
| Comparatve Example 9 | 11 | 180 | <1 | — | — | — |

TABLE 8

| | Carbon dioxide concentration in TMAH [ppm by mass] | Amine concentration [ppm by mass] | | | | pH | | |
|---|---|---|---|---|---|---|---|---|
| | | Preparation step | During reaction step | Immediately after pdoduction | After 30 days | During reaction step | Immediately after pdoduction | During storage |
| Example 21 | <1 | 5 | 5 | 5 | 5 | 13.4 | 13.0 | 13.0 |
| Example 22 | <1 | 5 | 5 | 5 | 5 | 13.2 | 12.5 | 12.5 |
| Example 23 | <1 | 5 | 5 | 5 | 5 | 13.7 | 13.5 | 13.5 |
| Example 24 | <1 | 5 | 5 | 5 | 5 | 13.4 | 13.0 | 13.0 |
| Example 25 | <1 | 5 | 5 | 5 | 5 | 13.4 | 13.0 | 13.0 |
| Example 26 | <1 | 5 | 5 | 5 | 5 | 13.4 | 13.0 | 13.0 |
| Example 27 | <1 | 5 | 5 | 5 | 5 | 13.4 | 13.0 | 13.0 |
| Example 28 | <1 | 5 | 5 | 5 | 5 | >14.0 | >14.0 | 13.0 |
| Comparative Example 9 | <1 | 5 | 5 | 5 | 5 | 11.7 | 9.5 | 9.5 |

| | pH | | Hypochlorite ion concentration [% by mass] | | | Ru etching evaluation | |
|---|---|---|---|---|---|---|---|
| | After dilution After 30 days | (During use) | Immediately after pdoduction | After 30 days | Storage stability | [Å/min] | Favorable/ Unfavorable |
| Example 21 | 13.0 | 9.5 | 1.59 | 1.59 | Excellent | 346 | Favorable |
| Example 22 | 12.5 | 9.5 | 1.59 | 1.59 | Excellent | 344 | Favorable |
| Example 23 | 13.5 | 9.5 | 1.58 | 1.58 | Excellent | 343 | Favorable |
| Example 24 | 13.0 | 9.5 | 1.59 | 1.59 | Excellent | 341 | Favorable |
| Example 25 | 13.0 | 9.5 | 1.59 | 1.59 | Excellent | 342 | Favorable |

TABLE 8-continued

| | | | | | | | |
|---|---|---|---|---|---|---|---|
| Example 26 | 13.0 | 11.0 | 1.59 | 1.59 | Excellent | 19 | Favorable |
| Example 27 | 13.0 | 10.5 | 1.59 | 1.59 | Excellent | 53 | Favorable |
| Example 28 | 13.0 | 9.5 | 1.45 | 1.45 | Excellent | 300 | Favorable |
| Comparative Example 9 | 9.1 | 9.1 | 1.55 | 0.55 | Good | 65 | Unfavorable |

REFERENCE SIGNS LIST

10 Ice water
11 Three-necked flask
12 Thermometer protection tube
13 Thermocouple
14 Rotor
15 PFA tube
16 Gas washing bottle
17 5% by mass sodium hydroxide aqueous solution
18 Flowmeter
19 Water bath
21 Glass beaker
22 Thermometer protection tube
23 Thermocouple
24 Rotor
25 PFA tube
26 Flowmeter
27 Water bath
28 Ice water
31 Reaction apparatus
32 Reaction vessel
33 Quaternary alkyl ammonium hydroxide solution (before reaction)
34 Inner surface of reaction vessel
35 Thermometer
36 Stirring motor
37 Stirring rod
38 Stirring blade
39 Chlorine gas supply tube
40 Gas introduction tube
41 Nitrogen gas supply tube
42 Reaction liquid transfer tube
43 Pump
44 Filtration filter
45 Reaction liquid return tube
46 Chlorine gas outlet tube
47 Chlorine gas trap
48 Reaction bath
49 Half-joint

What is claimed is:

1. A method of producing a quaternary alkyl ammonium hypochlorite solution, the method comprising:
a preparation step in which a quaternary alkyl ammonium hydroxide solution is prepared and the concentration of amines in the quaternary alkyl ammonium hydroxide solution is set to 20 ppm by mass or less; and
a reaction step in which the quaternary alkyl ammonium hydroxide solution is brought into contact with chlorine gas, wherein
the pH of a liquid phase in the reaction step is 10.5 or more.

2. The method of producing a quaternary alkyl ammonium hypochlorite solution according to claim 1, wherein chlorine gas is contacted while maintaining the concentration of amines contained in the liquid phase in the reaction step at 100 ppm by mass or less.

3. The method of producing a quaternary alkyl ammonium hypochlorite solution according to claim 1, wherein the carbon dioxide concentration in the quaternary alkyl ammonium hydroxide solution is 0.001 ppm by mass or more and 500 ppm by mass or less.

4. The method of producing a quaternary alkyl ammonium hypochlorite solution according to claim 1, wherein the water content of the chlorine gas is 10 ppm by volume or less.

5. The method of producing a quaternary alkyl ammonium hypochlorite solution according to claim 1, wherein the reaction temperature is −35° C. or more and 25° C. or less in the reaction step.

6. The method of producing a quaternary alkyl ammonium hypochlorite solution according to claim 1, wherein the quaternary alkyl ammonium hydroxide solution prepared in the preparation step is a solution of a quaternary alkyl ammonium hydroxide in which the number of carbon atoms of the alkyl group is from 1 to 10.

7. The method of producing a quaternary alkyl ammonium hypochlorite solution according to claim 1, wherein
the reaction step is a step of bringing a quaternary alkyl ammonium hydroxide solution into contact with chlorine gas in a reaction vessel, wherein the surface of the reaction vessel in contact with the quaternary alkyl ammonium hydroxide solution is made of an organic polymer material, and the reaction vessel is shielded from light.

8. The method of producing a quaternary alkyl ammonium hypochlorite solution according to claim 7, wherein the organic polymer material is a fluororesin.

9. The method of producing a quaternary alkyl ammonium hypochlorite solution according to claim 1, the method further comprising a filtration step in which a quaternary alkyl ammonium hypochlorite solution is obtained by the production method according to claim 1, and then the resulting quaternary alkyl ammonium hypochlorite solution is filtered.

10. The method according to claim 9, wherein the pH of a quaternary alkyl ammonium hypochlorite solution in a filtration step at 25° C. is 13.5 or less.

11. The method of producing a quaternary alkyl ammonium hypochlorite solution according to claim 1, the method comprising a storage step in which a quaternary alkyl ammonium hypochlorite solution is obtained by the production method according to claim 1, and the resulting quaternary alkyl ammonium hypochlorite solution is stored under shade of light with a pH of the quaternary alkyl ammonium hypochlorite solution at a temperature of 25° C. of 12.0 or more and less than 14.0.

12. The method of producing a quaternary alkyl ammonium hypochlorite solution according to claim 11, wherein the concentration of amines in a quaternary alkyl ammonium hypochlorite solution is stored at a concentration of 100 ppm by mass or less in the storage step.

* * * * *